US012595463B2

(12) United States Patent
Bhumiratana et al.

(10) Patent No.: US 12,595,463 B2
(45) Date of Patent: Apr. 7, 2026

(54) INJECTABLE OFF-THE-SHELF CARTILAGE, TENDON, AND LIGAMENT REPAIR COMPOSITIONS AND METHODS OF USE

(71) Applicant: EPIBONE, INC., Long Island City, NY (US)

(72) Inventors: Sarindr Bhumiratana, Oceanside, NY (US); Terri-Ann Kelly, Springfield, MA (US); Eric Meade Jeffries, Warrington, PA (US); Olivia Spencer Beane, Rahway, NJ (US); Angela Hai Huang, Flushing, NY (US)

(73) Assignee: EPIBONE, INC., Long Island City, NY (US)

( * ) Notice: Subject to any disclaimer, the term of this patent is extended or adjusted under 35 U.S.C. 154(b) by 57 days.

(21) Appl. No.: 17/716,029

(22) Filed: Apr. 8, 2022

(65) Prior Publication Data

US 2022/0228109 A1    Jul. 21, 2022

Related U.S. Application Data

(63) Continuation of application No. 16/978,407, filed as application No. PCT/US2019/020893 on Mar. 6, 2019.

(Continued)

(51) Int. Cl.
*C12N 5/00* (2006.01)
*A61K 9/00* (2006.01)
(Continued)

(52) U.S. Cl.
CPC .......... *C12N 5/0068* (2013.01); *A61K 9/0019* (2013.01); *A61K 9/06* (2013.01);
(Continued)

(58) Field of Classification Search
CPC .... C12N 5/0068; C12N 5/0655; C12N 5/066; A61K 9/0019; A61K 9/06; A61K 9/5031;
(Continued)

(56) References Cited

U.S. PATENT DOCUMENTS 6,153,432 A    11/2000  Halvorsen et al.
8,734,827 B2    5/2014  Chan et al.
(Continued)

FOREIGN PATENT DOCUMENTS

CN        101011600 A    8/2007
CN        104307046 A    1/2015
(Continued)

OTHER PUBLICATIONS

Supporting info for Bhumiratana, Sarindr et al. "Large, stratified, and mechanically functional human cartilage grown in vitro by mesenchymal condensation." Proceedings of the National Academy of Sciences of the United States of America vol. 111,19 (2014): 6940-5), (Provided in IDS of Apr. 8, 2022) (Year: 2014).*
(Continued)

*Primary Examiner* — Tracy Vivlemore
*Assistant Examiner* — Thomas R. Amick
(74) *Attorney, Agent, or Firm* — Troutman Pepper Locke LLP

(57) ABSTRACT

Compositions comprising a condensed mesenchymal cell body and a hydrogel are provided. The compositions may further include drugs or growth factors. The condensed mesenchymal cell body may include a connective tissue cell, or even a progenitor cell capable of producing connective tissue extracellular matrices such collagen and glycosaminoglycan. Also provided are methods of treating connective tissue defects, cartilage injury, and cartilage degradation.

11 Claims, 20 Drawing Sheets

Related U.S. Application Data

(60) Provisional application No. 62/639,322, filed on Mar. 6, 2018.

(51) Int. Cl.

| | |
|---|---|
| *A61K 9/06* | (2006.01) |
| *A61K 9/50* | (2006.01) |
| *A61K 31/726* | (2006.01) |
| *A61K 38/18* | (2006.01) |
| *A61K 38/39* | (2006.01) |
| *A61L 27/18* | (2006.01) |
| *A61L 27/20* | (2006.01) |
| *A61L 27/24* | (2006.01) |
| *A61L 27/36* | (2006.01) |
| *A61L 27/38* | (2006.01) |
| *A61L 27/52* | (2006.01) |
| *A61L 27/54* | (2006.01) |
| *C12N 5/077* | (2010.01) |

(52) U.S. Cl.
CPC .......... *A61K 9/5031* (2013.01); *A61K 31/726* (2013.01); *A61K 38/1841* (2013.01); *A61K 38/39* (2013.01); *A61L 27/18* (2013.01); *A61L 27/20* (2013.01); *A61L 27/24* (2013.01); *A61L 27/3654* (2013.01); *A61L 27/3662* (2013.01); *A61L 27/3852* (2013.01); *A61L 27/386* (2013.01); *A61L 27/52* (2013.01); *A61L 27/54* (2013.01); *C12N 5/0655* (2013.01); *C12N 5/066* (2013.01); *A61L 2400/06* (2013.01); *A61L 2430/06* (2013.01); *A61L 2430/10* (2013.01); *C12N 2501/15* (2013.01); *C12N 2501/90* (2013.01); *C12N 2501/998* (2013.01); *C12N 2533/40* (2013.01)

(58) Field of Classification Search
CPC .. A61K 31/726; A61K 38/1841; A61K 38/39; A61L 27/18; A61L 27/20; A61L 27/24; A61L 27/3654; A61L 27/3662; A61L 27/3852; A61L 27/386; A61L 27/52; A61L 27/54; A61L 2400/06; A61L 2430/06
See application file for complete search history.

(56) References Cited

U.S. PATENT DOCUMENTS

| | | | |
|---|---|---|---|
| 2010/0099190 A1 | 4/2010 | Wang et al. |
| 2010/0120149 A1 | 5/2010 | Kim et al. |
| 2012/0076878 A1 | 3/2012 | Li et al. |
| 2014/0148915 A1 | 5/2014 | Aljitawi et al. |
| 2015/0166960 A1 | 6/2015 | Lehmann et al. |
| 2016/0129155 A1 | 5/2016 | Lin et al. |
| 2017/0049936 A1 | 2/2017 | Reves et al. |
| 2017/0333597 A1 | 11/2017 | Bhumiratana et al. |

FOREIGN PATENT DOCUMENTS

| | | |
|---|---|---|
| CN | 107648668 A | 2/2018 |
| JP | 2010-525810 A | 7/2010 |
| JP | 2017-529362 | 10/2017 |
| JP | 2017-532008 A | 11/2017 |
| WO | 2003/080822 A1 | 10/2003 |
| WO | 2010/102059 A1 | 9/2010 |
| WO | 2014/172575 A1 | 10/2014 |
| WO | 2016/118604 A1 | 7/2016 |
| WO | 2016/180789 A1 | 11/2016 |
| WO | 2016/193175 A1 | 12/2016 |
| WO | 2017/151619 A1 | 9/2017 |
| WO | 2017/187941 A1 | 11/2017 |

OTHER PUBLICATIONS

Moioli, Eduardo K et al. "Sustained release of TGFbeta3 from PLGA microspheres and its effect on early osteogenic differentiation of human mesenchymal stem cells." Tissue engineering vol. 12,3 (2006): 537-46 (Year: 2006).*

Irene Ginis, et al. Evaluation of Bone Marrow-Derived Mesenchymal Stem Cells After Cryopreservation and Hypothermic Storage in Clinically Safe Medium. Tissue Engineering Part C: Methods. Jun. 2012.453-463. (Year: 2012).*

Japanese Office Action issued in JP Application No. 2020-546395 dated Nov. 7, 2022.

Gimble et al., "Adipose-Derived Stromal/Stem Cells: A Primer" Organogenesis, 2013, vol. 9, Issue 1, pp. 1-8.

Ng et al., "Duty Cycle of Deformational Loading Influences the Growth of Engineered Articular Cartilage", Cell Mol. Bloeng., Sep. 1, 2009, vol. 2, No. 3, pp. 386-394.

Riboh et al., "Comparative efficacy of cartilage repair procedures in the knee: a network meta-analysis", Knee Surg. Sports Traumatol. Arthrosc., 2016, vol. 25, pp. 3786-3799.

Goyal et al., "Evidence-based status of microfracture technique: a systematic review of level I and II studies", Arthroscopy, 2013, vol. 29, No. 9, pp. 1579-1588.

Brittberg et al., "Rabbit articular cartilage defects treated with autologous cultured chondrocytes", Clin. Orthop., 1996, No. 326, pp. 270-283.

Jacobi et al., "MACI—a new era?", Sports Med Arthrosc. Rehabil. Ther. Technol., 2011, vol. 3, No. 1, p. 10.

Hangody et al., "Arthroscopic autogenous osteochondral mosaicplasty for the treatment of femoral condylar articular defects. A preliminary report", Knee Surg. Sports Traumatol. Arthrosc., 1997, 5(4): p. 262-267.

O'Driscoll et al., "The chondrogenic potential of free autogenous periosteal grafts for biological resurfacing of major full-thickness defects in joint surfaces under the influence of continuous passive motion. An experimental investigation in the rabbit", Journal of Bone and Joint Surgery, 1986, vol. 68-A, No. 7, p. 1017-1035.

Bobic, "Current Status of the Articular Cartilage Repair", The Journal of Regenerative Medicine, 2000, 1(4): p. 37-41.

McNickle et al., "Overview of Existing Cartilage Repair Technology", Sports Med. Arthrosc. Rev., 2008, vol. 16, No. 4, pp. 196-201.

Bobic, V., "Tissue Repair Techniques of the Future: Options for Articular Cartilage Injury", Conference Report. Medscape Orthopaedics & Sports Medicine eJournal, 2000, vol. 4, No. 1, 8 pages.

Bos et al., "Articular cartilage repair and the evolving role of regenerative medicine", Open Access Surgery, 2010, vol. 3, pp. 109-122.

Rivera et al., "Posttraumatic Osteoarthritis Caused by Battlefield Injuries: The Primary Source of Disability in Warriors", J. Am. Acad. Orthop. Surg., 2012, vol. 20, Supplement 1, pp. S64-S69.

Anderson et al., "Post-traumatic osteoarthritis: Improved understanding and opportunities for early intervention", J. Orthop. Res, 2011, vol. 29, No. 6, pp. 802-809.

Hangody et al., "Autologous osteochondral grafting—technique and long-term results", Int. J. Care Injured, 2008. 39(1): p. S32-S39.

Eichinger et al., "Penetrating Blast Injury to the Knee of a United States Soldier Treated with Allograft Mosaicplasty", Cartilage, 2011, vol. 2, No. 3, pp. 307-311.

Scully et al., "Allograft Osteochondral Transplantation in the Knee in the Active Duty Population", Military Medicine, 2011, vol. 176, No. 10, pp. 1196-1201.

Lima et al., "Functional tissue engineering of chondral and osteochondral constructs", Biorheology, 2004, 41(3-4): pp. 577-590.

Hu et al., "A self-assembling process in articular cartilage tissue engineering", Tissue Engineering, 2006, vol. 12, No. 4, p. 969-979.

Bhumiratana et al., "Large, stratified, and mechanically functional human cartilage grown in vitro by mesenchymal condensation", Proc. Natl. Acad. Sci. U S A, 2014, vol. 111, No. 19, pp. 6940-6945.

McIntosh et al., "Evolution and future prospects of adipose-derived immunomodulatory cell therapeutics", Expert Rev. Clin. Immunol., 2013, vol. 9, No. 2, pp. 175-184.

(56) References Cited

OTHER PUBLICATIONS

Yodmuang et al., "Synergistic effects of hypoxia and morphogenetic factors on early chondrogenic commitment of human embryonic stem cells in embryoid body culture", Stem Cell Rev., 2015, vol. 11, No. 2, pp. 228-241.

Ryan et al., "Mesenchymal stem cells avoid allogeneic rejection", Journal of Inflammation, 2005, vol. 2, No. 8, 11 pages.

International Search Report and Written Opinion issued in International Application No. PCT/US2019/020893 dated May 28, 2019.

Bhumiratana et al. "Engineering Physiologically Stiff and Stratified Human Cartilage by Fusing Condensed Mesenchymal Stem Cells," Methods, Mar. 28, 2015 (Mar. 28, 2015), vol. 84, pp. 109-114.

Park et al., "Effect of growth factors on chondrogenic differentiation of rabbit mesenchymal cells embedded in injectable hydrogels", Journal of Bioscience and Bioengineering, 2008, vol. 106, No. 1, pp. 74-79.

Gurkan et al., "Engineering Anisotropic Biomimetic Fibrocartilage Microenvironment by Bioprinting Mesenchymal Stem Cells in Nanoliter Gel Droplets", Molecular Pharmaceutics, 2014, vol. 11, No. 7, pp. 2151-2159.

Gugjoo et al., "Cartilage tissue engineering: Role of mesenchymal stem cells along with growth factors & scaffolds", Indian Journal of Medical Research, 2016, vol. 144, No. 3, pp. 339-347.

European Search Report issued in EP Application No. 19763750.7 dated Nov. 24, 2021.

Le Blanc et al., "HLA expression and immunologic properties of differentiated and undifferentiated mesenchymal stem cells", Experimental Hematology, 2003, vol. 31, Issue 10, pp. 890-896.

Junior et al., "Study of mesenchymal stem cells cultured on a poly(lactic-co-glycolic acid) scaffold containing simvastatin for bone healing", Journal of Applied Biomaterials & Functional Materials, 2017, vol. 15, No. 2, pp. e133-e141.

Motoike et al., "Cryopreserved clumps of mesenchymal stem cell/extracellular matrix complexes retain osteogenic capacity and induce bone regeneration", Stem Cell Research & Therapy, 2018, vol. 9, 73, pp. 1-13.

Sato et al., "Direct transplantation of mesenchymal stem cells into the knee joints of Hartley strain guinea pigs with spontaneous osteoarthritis", Arthritis Research & Therapy, 2012, vol. 14, R31, p. 1-9.

Yamasaki et al., "Bone regeneration by using marrow-derived-cell aggregates", Proceedings of the 21th Bioengineering Conference, 2008, vol. 20th, pp. 351-352, 4 pages.

Kishi et al., "The mechanism to obtain undifferentiated ability by making aggregate", Grant-in-Aid for Scientific Research Subsidies Research Result Report Keio University Scientific Information Repository, 2015, 5 pages, with English Abstract. https://koara.lib.keio.ac.jp/xoonips/modules/xoonips/detail.php?koara_id=KAKEN_25670754selka.

Shao et al., "Chondrogenesis of human bone marrow mesenchymal cells by transforming growth factors [beta]1 through cell shape changes on controlled biomaterials", Journal of Biomedical Materials Research. Part A, 2012, vol. 100, No. 12, pp. 3344-3352.

Jiang et al., "Spheroldal formation preserves human stem cells for prolonged time under ambient conditions for facile storage and transportation", Biomaterials, 2017, vol. 133, pp. 275-286.

Sart et al., "Cryopreservation of Pluripotent Stem Cells Aggregates in Defind Protein-Free Formulation", Biotechnol. Prog., 2013, vol. 29, No. 1, pp. 143-153, DOI:10.1002-/btpr.1653.

Wang et al., "Scalable expansion of human induced pluripotent stem cells in the defind xeno-free E8 medium under adherrent and suspension culture conditions", Stem Cell Research, 2013, vol. 11, pp. 1103-1116.

Office Action issued in Japanese Patent Application No. 2020-546395 dated Mar. 22, 2023 (with English translation).

Office Action issued in Japanese Patent Application No. 2020-546395 dated Dec. 11, 2023 (with English translation).

Office Action issued in Chinese Application No. 201980029823.8 dated Apr. 28, 2023 (with English translation).

Office Action issued in Chinese Application No. 201980029823.8 dated Feb. 2, 2024 (with English translation).

Korean Office Action issued in KR Application No. 10-2020-7028571 dated Jul. 29, 2025 (with machine translation).

* cited by examiner

Population doubling time (PDT) of ADSCs

Immunogenicity dataset for a typical donor

Immunogenicity Marker

Negative Controls

Positive Controls

| | Collagen (Col) | 1:1 (Col:Hy) | 1:4 (Col:Hy) | Hyaluronate (Hy) |
|---|---|---|---|---|
| Wet Weight (mg) | 7.5 | 5.9 | 5.3 | 11.9 |
| DNA (µg/mg wet weight) | 208 | 208 | 201 | 142 |
| GAG (% wet weight) | 1.5 | 1.1 | 1.1 | 0.9 |
| Collagen (% wet weight) | 1.2 | 1.4 | 1.5 | 0.8 |

| Group | # Cells | Wet Weight (mg) | DNA (ug/mg) | GAG (% wet weight) | Collagen (% wet weight) |
|-------|---------|-----------------|-------------|--------------------|--------------------------|
| A | 250k | 13.7±2.7 (n=2) | 1.3±0.3 (n=2) | 4.1±0.1 (n=2) | 1.8±0.2 (n=2) |
| B | 100k | 15.0±6.1 (n=3) | 0.9±0.1 (n=2) | 3.1±0.3 (n=2) | 1.6±0.4 (n=2) |
| C | 50k | 17.9±0.6 (n=3) | 0.9±0.1 (n=3) | 3.2±0.4 (n=3) | 1.6±0.2 (n=3) |

*FIG. 15C*

INJECTABLE OFF-THE-SHELF CARTILAGE, TENDON, AND LIGAMENT REPAIR COMPOSITIONS AND METHODS OF USE

CROSS-REFERENCE TO RELATED APPLICATIONS

This application is a continuation of U.S. application Ser. No. 16/978,407, filed Sep. 4, 2020, which is a U.S. National Phase of PCT/US2019/020893, filed Mar. 6, 2019, which claims priority to U.S. Provisional Application No. 62/639,322, filed on Mar. 6, 2018. The disclosures of each are incorporated by reference herein in their entireties.

BACKGROUND

Cartilage injuries affect approximately one million Americans annually, resulting in more than 500K cartilage-related procedures [1]. Current methods of treating cartilage injuries include debridement and microfracture [2], marrow stimulation, autologous chondrocyte implantation (ACI) [3], matrix-induced autologous chondrocyte implantation (MACI) [4], mosaicplasty [5], osteochondral autografting and osteochondral allografting [6-8]. There are at least 350,000 knee arthroplasties performed each year, with chondral lesions present in >60% of cases [9]. The number of such procedures is forecasted to increase due to population growth, longevity and advances in diagnosis tools.

Cartilage lesions are frequently associated with other articular injuries, and can progress to joint degeneration and osteoarthritis (OA) [10]. OA affects about 20% of Americans, with 10% of those with OA having activity limitations. Annual costs from OA are estimated to exceed $130 billion. The World Health Organization ranked OA as the fourth condition in terms of impact on disease-free life-years and disability, while the Centers for Disease Control and Prevention determined that arthritis is the number-one cause of disability in the United States [11]. Osteoarthritis even affects younger people as post-traumatic osteoarthritis (PTOA) [12]. PTOA is estimated to cause 12% of symptomatic arthritis of the hip and knee, with associated costs of over $3 billion per year. PTOA and other common cartilage injuries particularly affect the active duty military population, which has about ten times the incidence of all common cartilage injuries as compared to civilians. As an example, ACL and meniscus injuries affect 3.65 and ~6.5 out of 1000 soldiers, respectively, every year. The corresponding rates for civilians are ~0.34 and ~0.45 out of 1000 [13]. There is a great need to treat PTOA and cartilage injuries in the military population and in younger people.

The most common procedures to treat osteochondral defects are microfracture, mosaicplasty, allograft or autograft osteochondral grafting, ACI, and, more recently, MACI. All techniques suffer from several drawbacks that are affected by size limitations, the patient's age, and quality of surrounding cartilage. Drawbacks include reduced biomechanical properties, long recovery, double surgeries and need for donor tissues. Success rates tend to be low and there is a high risk for failures 1-5 years post-surgery.

Autograft and allograft transplantations have been used to treat cartilage injuries. Autograft has been shown to be effective in lesions up to 3 cm in diameter, with good-to-excellent outcomes reported even among athletes [14]. Allograft osteochondral transplantation has previously been utilized in combat soldiers, allowing them to return to their military position [15]. However, allograft osteochondral transplantation has proven to be less successful in active duty military populations when compared to civilians. A retrospective review analyzed the effectiveness of allograft osteochondral transplantation in the knee in the active duty population, focusing on ability of patients to return to their status following the procedure [16]. Although this method of surgery for large lesions of the knee has a good rate of success among civilian patients, it failed to ensure retention on active duty for injured soldiers, particularly when they occupy a physically demanding military position. Many patients treated by allograft osteochondral transplantation have not been able to remain on active duty in their previous role. There is a need for improved transplantation therapies for those in the military who would otherwise have few alternative options in the military. There is also a need for improved transplantation therapies for those who lead a comparably physically active lifestyle, such as professional and amateur athletes, firefighters and police officers.

Improvements are still needed in preparing cartilage for transplantation. For a long time, cartilage has been a major focus of the field of tissue engineering, both due to the strong clinical need, the avascular nature of this tissue and low cell density. Cartilage tissue engineering has progressed mostly by utilizing primary chondrocytes extracted from native cartilage. These highly active, yet phenotypically stable and mature, cells could produce cartilaginous matrix. Even simple culture systems enabled engineering of viable cartilaginous tissue constructs from primary chondrocytes that are a few millimeters thick. Also, cultivation in bioreactors with a dynamic flow environment yielded cartilage with similar biochemical composition and mechanical stiffness as parent cartilage. In cartilage tissue engineering, juvenile bovine chondrocytes have been used in conjunction with scaffolding materials to engineer cartilage with mechanical properties approximating those of native tissue [17, 18]. These methods however suffer from limited availability, and limited ability to generate functional cartilage from adult chondrocytes.

In addition to cartilage injuries, connective tissue injuries are a persistent clinical challenge. In the U.S., damaged tendons, ligaments, and joint capsules account for 45% of the reported 32 million musculoskeletal injuries each year. Moreover, these incidence rates are rising due to increased sports participation and an aging population. Connective tissues are notoriously difficult to repair. Current treatment strategies often include surgical reconstruction with bone-tendon-bone autografts, such as the patella tendon. This multi-tissue composition improves fixation and integration to host tissue. However, these autografts do not adequately mimic the original tissues and fail to restore pre-injury tissue function, complex biochemical properties, and enthesis structure. Consequently, autograft procedures are associated with high failure rates and require revision surgery, compromising patient quality of life.

Progenitor stem cells have the potential to form cartilaginous and connective tissue. Many attempts to engineer cartilage and connective tissues from stem cells have been investigated with a goal to fully regenerate cartilage with native form and function. Cartilage-like tissue can be grown in vitro starting from mesenchymal stem cells [19] or chondrocytes, such as Neocart and MACI. The use of these products, however, requires invasive surgery for administration. There has not yet been a successful product that aims to regenerate cartilage and connective tissues with a minimally invasive procedure, such as arthroscopic surgery, or that are readily available off-the-shelf.

In view of the above, there is a need to provide improved compositions of product to treat cartilage and/or osteochondral defects by regenerating native-like tissue.

SUMMARY OF THE INVENTION

Described herein are improved compositions and methods to regenerate skeletal and connective tissue such as cartilage, tendons, and ligaments to be used as treatment modalities for multiple ranges of defects such as chondral/osteochondral defects, tears or ruptures of cartilage, meniscal tissue, ligaments, tendons and muscle that occurred due to various causes such as trauma, tissue degeneration, post-traumatic osteoarthritis, arthritis, etc.

The compositions and methods described herein include a novel and improved approach to the treatment of connective tissue defects, such as articular or non-articular cartilage defects, tendon defects, and ligament defects. Advantages include: (1) an injectable platform that allows implantation into a wide variety of defect sizes and geometries; (2) ease of use and precise filling of the defect; (3) progenitor cells that can undergo chondrogenesis, tendogenesis, tissuegenesis and form native tissue-like architecture, which is important for durable function; (4) ability of cells to develop into native-like tissue with biomechanical properties (compressive modulus, friction coefficient, tensile strength, and shear strength); (5) in vivo maturation of condensed mesenchymal bodies generated from cells to allow the formation of seamless, mechanically competent interface with the host tissues; and (6) an off-the-shelf cell-based tissue product that may be readily available for on-demand treatment of traumatic cartilage and connective tissue injuries. The cells are viable throughout culture and before and after injection or implantation. Tissue integration to the host is promoted. Repeated surgeries and tissue morbidity may be avoided, along with improvements in clinical outcomes and reduced recovery times.

In one aspect is provided a composition comprising a condensed mesenchymal cell body (CMB) and a hydrogel. The CMB may be generated from cells that can undergo chondrogenesis. Alternatively, the CMB may be generated from cells that form connective tissue. The connective tissue may comprise collagen, proteoglycans, hyaluronic acid or elastin. The collagen may include type I, II, III, IV, V, VI, VII, VIII, IX, X or XI collagen. Proteoglycans may include glycosaminoglycan, heparan sulfate, or chondroitin sulfate. The CMB may develop into tissue comprising various types of extracellular matrix (ECM). The ECM may comprise, for example, collagen, glycosaminoglycan, elastin, fibronectin, and/or laminin. The composition may optionally comprise one or more drugs or growth factors, depending on which connective type is being generated.

In some embodiments, the composition further comprises a polymer microsphere, wherein one or more of the growth factors is encapsulated in the polymer microsphere. In some embodiments, the polymer microsphere comprises poly(lactic-co-glycolic acid) (PLGA), poly(lactic acid) (PLA), or a combination of PLGA and PLA. In some embodiments, the CMB comprises a cell selected from a connective tissue cell and a progenitor cell capable of forming a cartilage cell, a tendon cell, a ligament cell, or a meniscal cell. In some embodiments, the CMB comprises a cell isolated from cartilage, tendon, ligament, or meniscus. In some embodiments, the cell is a tenocyte, a tenoblast, a fibrocyte or a fibroblast. In some embodiments, the CMB is a chondrocyte, a progenitor cell selected from mesenchymal stem cells (MSC), an embryonic stem cell (ESC), induced pluripotent stem cells (iPS) or the cells that are extracted from native tissues such as cartilage, tendon, ligament, and meniscus which include but not limited to tenocytes, tenoblast, fibrocytes, fibroblasts. In some embodiments, the CMB comprises a stem cell. In some embodiments, the stem cell is selected from a mesenchymal stem cell (MSC), adipose-derived stem cell (ADSC), bone-marrow derived stem cell (BMSC), umbilical cord blood stem cell (UB-MSC), a neural-crest stem cell, an induced pluripotent stem cell, an embryonic stem cell, a primary chondrocyte, and a neural-crest stem cell.

In some embodiments, the cell or the stem cell (e.g., MSC, ADSC, BMSC, or UB-MSC) is from an allogenic source or autologous source. In some embodiments, the cell or the stem cell (e.g., MSC, ADSC, BMSC, or UB-MSC) is anti-immunogenic and/or immunosuppressant (see, e.g., Gimble, J. M. et al., "Adipose-Derived Stromal/Stem Cells: A Primer" Organogenesis, 2013, 9(1):3-10.) In some embodiments, the CMB and/or cells are cryopreserved or stored at a temperature of about −80° C. or less than about −80° C. for at least about one day. In some embodiments, the CMB and/or cells are cryopreserved or stored at a temperature of about −196° C. or less than about −196° C. for at least about one day, about two days, about three days, about four days, about five days, about six days, or about one week. In some embodiments, the CMB and/or cells are cryopreserved, or stored at a subzero temperature of between −1° C. to −25° C., or less than about −1° C., for at least about one day, about two days, about three days, about four days, about five days, about six days, or about one week. In some embodiments, the CMB are stored at about −20° C., at −20° C., or at less than about −20° C., for at least one day, about two days, about three days, about four days, about five days, about six days, or about one week. In some embodiments, the CMB are stored at about −10° C., at −10° C., or at less than about −10° C., for at least one day, about two days, about three days, about four days, about five days, about six days, or about one week. In some embodiments, the CMB and/or cells are hypothermically preserved, or stored at a temperature of between 1° C. to 30° C., or less than about 30° C., for at least about one day, about two days, about three days, about four days, about five days, about six days, or about one week. In some embodiments, the CMB are stored at about 4° C., at 4° C., or at less than about 4° C., for at least one day, about two days, about three days, about four days, about five days, about six days, or about one week. In some embodiments, the CMB are stored at about 25° C., at 25° C., or at less than about 25° C., for at least one day, about two days, about three days, about four days, about five days, about six days, or about one week.

In some embodiments, cells in the CMB do not express a substantial or detectable amount of human leukocyte antigen (HLA) class II, CD40, CD80, or CD86 on the cell surface. In some embodiments, cells in the CMB do not express a substantial or detectable amount of human leukocyte antigen (HLA) class II, CD40, CD80, or CD86 on the cell surface according to an immunoassay, for example an assay including one or more of flow cytometry, ELISPOT, quantitative PCR, and mixed lymphocyte reaction assays.

In some embodiments, cells in the CMB express a substantial amount of CD73, CD90, CD105, or CD146 on the cell surface. In some embodiments, cells in the CMB express a detectable amount of CD73, CD90, CD105, or CD146 on the cell surface. In some embodiments, cells in the CMB do not express a substantial amount of CD73, CD90, CD105, or CD146 on the cell surface according to an immunoassay, for example an assay including one or more of flow cytometry, ELISPOT, quantitative PCR, and mixed lymphocyte reaction assays. In some embodiments, cells in the CMB do not express a detectable amount of CD73, CD90, CD105, or CD146 on the cell surface according to an immunoassay, for example an assay including one or more of flow cytometry, ELISPOT, quantitative PCR, and mixed lymphocyte reaction assays.

In some embodiments, the hydrogel is selected from fibrin glue, platelet-rich plasma (PRP), type I collagen, type II collagen, chitosan, gelatin, polyethylene glycol diacrylate, hyaluronic acid, and any combination of fibrin glue, PRP, type I collagen, type II collagen, chitosan, gelatin, polyethylene glycol diacrylate, and hyaluronic acid. In some embodiments, the growth factor is selected from TGF-β superfamily members which include TGF-β1, TGF-β2, TGF-β3, TGF-β4, BMP-1, BMP-2, BMP-3, BMP-4, BMP-5, BMP-6, BMP-7, BMP-8. In some embodiments, the growth factor is selected from TGF-β superfamily members which include TGF-β1, TGF-β2, TGF-β3, TGF-β4, BMP-1, BMP-2, BMP-3, BMP-4, BMP-5, BMP-6, BMP-7, BMP-8 and any combinations which have been shown to act synergistically (Choi, S. et al., Int. J. Oral. Sci., 2013, 5(1):7-13, and Hildner, F. et al., J. Biomed. Mater. Res. A, 2010, 94(3):978-87.)

In some embodiments, the growth factor is a TGF-β superfamily member. In some embodiments, the growth factor is a morphogenic protein selected from the group consisting of OP-1, OP-2, OP-3, TGF-β1, TGF-β2, TGF-β3, TGF-β4, BMP-1, BMP-2, BMP-3, BMP-4, BMP-5, BMP-6, BMP-8, BMP-9, BMP-10, BMP-11, BMP-12, BMP-13, BMP-15, BMP-16, BMP-17, BMP-18, DPP, CTGF, Vg1, Vgr-1, 60A protein, GDF-1, GDF-2, GDF-3, GDF-5, GDF-6, GDF-7, GDF-8, GDF-9, GDF-10, GDF-11, GDF-12, CDMP-1, CDMP-2, CDMP-3, NODAL, UNIVIN, SCREW, ADMP, NEURAL. In some embodiments, the composition further comprises one or more of insulin, transferrin, human serum albumin, proline, bovine serum albumin, selenic acid, linoleic acid, dexamethasone, and ascorbic acid.

In some embodiments, the cells in the CMB are in suspension.

In some embodiments, a CMB is created from at least 1,000 cells. In some embodiments, the CMB is generated from at least 5,000 cells, at least 10,000 cells, at least 15,000 cells, at least 20,000 cells, at least 25,000 cells, at least 30,000 cells, at least 40,000 cells, at least 50,000 cells, at least 60,000 cells, at least 70,000 cells, at least 80,000 cells, at least 90,000 cells, at least 100,000 cells, at least 125,000 cells, at least 150,000 cells, at least 175,000 cells, at least 200,000 cells, at least 225,000 cells, at least 250,000 cells, at least 300,000 cells, at least 400,000 cells, or at least 500,000 cells.

In some embodiments, CMBs are homogenous in size. For example, the CMBs may have a diameter of about 200 μm, about 300 μm, about 400 μm, about 500 μm, about 600 μm, about 800 μm, about 1 mm, about 1.2 mm, about 1.4 mm, about 1.6 mm, about 1.8 mm, about 2.0 mm, about 2.2 mm, about 2.4 mm, about 2.6 mm, about 2.8 mm, or about 3 mm.

In some embodiments, CMBs vary in size. The CMBs may have a diameter of from 200 μm to 3.0 mm. The CMBs may have a diameter of from 200 μm to 800 μm. The CMBs may have a diameter of from 400 μm to 1.0 mm. The CMBs may have a diameter of from 600 μm to 1.2 mm. The CMBs may have a diameter of from 800 μm to 1.6 mm. The CMBs may have a diameter of from 1.0 mm to 1.8 mm. The CMBs may have a diameter of from 1.2 mm to 2.0 mm. The CMBs may have a diameter of from 1.4 mm to 2.4 mm. The CMBs may have a diameter of from 2.0 mm to 3.0 mm.

In some embodiments, the composition is injectable.

In another aspect is provided a method of treating a cartilage defect in a patient comprising administering any of the compositions described above and herein into the cartilage or into the area surrounding the cartilage.

In another aspect is provided a method of preventing cartilage degradation or treating cartilage injury, a cartilage degenerative disease or a cartilage disorder in a patient comprising administering any of the compositions described above and herein into the cartilage or into the area surrounding the cartilage.

In some embodiments of the above methods, the cartilage is articular cartilage. In some embodiments of the above methods, the cartilage is non-articular cartilage. In some embodiments, the non-articular cartilage is selected from the group consisting of nasal cartilage, auricular cartilage, tracheobronchial cartilage, costal cartilage, meniscus and intervertebral disc. In some embodiments, the method is effective to form cartilage tissue comprising 1-20% (w/w) glycosaminoglycan (GAG) in the site of the cartilage defect, cartilage degradation, cartilage injury, cartilage degenerative disease or cartilage disorder. In some embodiments, the method is effective to form cartilage tissue comprising 0.5-20% (w/w) collagen. In some embodiments, the method is effective to form cartilage tissue comprising at least 1.2% (w/w), 1.3% (w/w), 1.4% (w/w), 1.5% (w/w), or 1.6% (w/w) collagen in the site of the cartilage defect, cartilage degradation, cartilage injury, cartilage degenerative disease or cartilage disorder. In some embodiments, the method is effective to form cartilage having a Young's modulus of at least 100 kPa and a friction coefficient of at most 0.8 in the site of the cartilage defect, cartilage degradation, cartilage injury, cartilage degenerative disease or cartilage disorder.

In some embodiments, the method is effective to form cartilage in the site of the cartilage defect, cartilage degradation, cartilage injury, cartilage degenerative disease or cartilage disorder, and wherein the cartilage is integrated with any adjacent cartilage and subchondral bone tissue at or surrounding the site.

In some embodiments, the method is effective to connect native tissue together in the site of tissue tear or rupture, tissue degeneration, injury, or degenerative disorder. In various embodiments, tissue such as tendon, ligament, meniscus, muscle is integrated with any adjacent tissue such as cartilage, bone, muscle, other connective tissues, or tissue of the same type.

In another aspect is provided a method of forming cartilage tissue in vitro or in vivo using any composition described herein.

In another aspect is provided a method of treating a torn or ruptured connective tissue in a patient comprising administering any of the above compositions into the torn or ruptured connective tissue or into an area surrounding the torn or ruptured connective tissue. In some embodiments, the connective tissue is a ligament, a tendon, or a meniscus.

BRIEF DESCRIPTION OF THE DRAWINGS

FIG. 15C shows quantitative characterization of cartilage constructs fabricated with various CMB sizes. Results reveal comparable wet weight and DNA, GAG, and collagen content among experimental groups.

DETAILED DESCRIPTION

Figure 1:
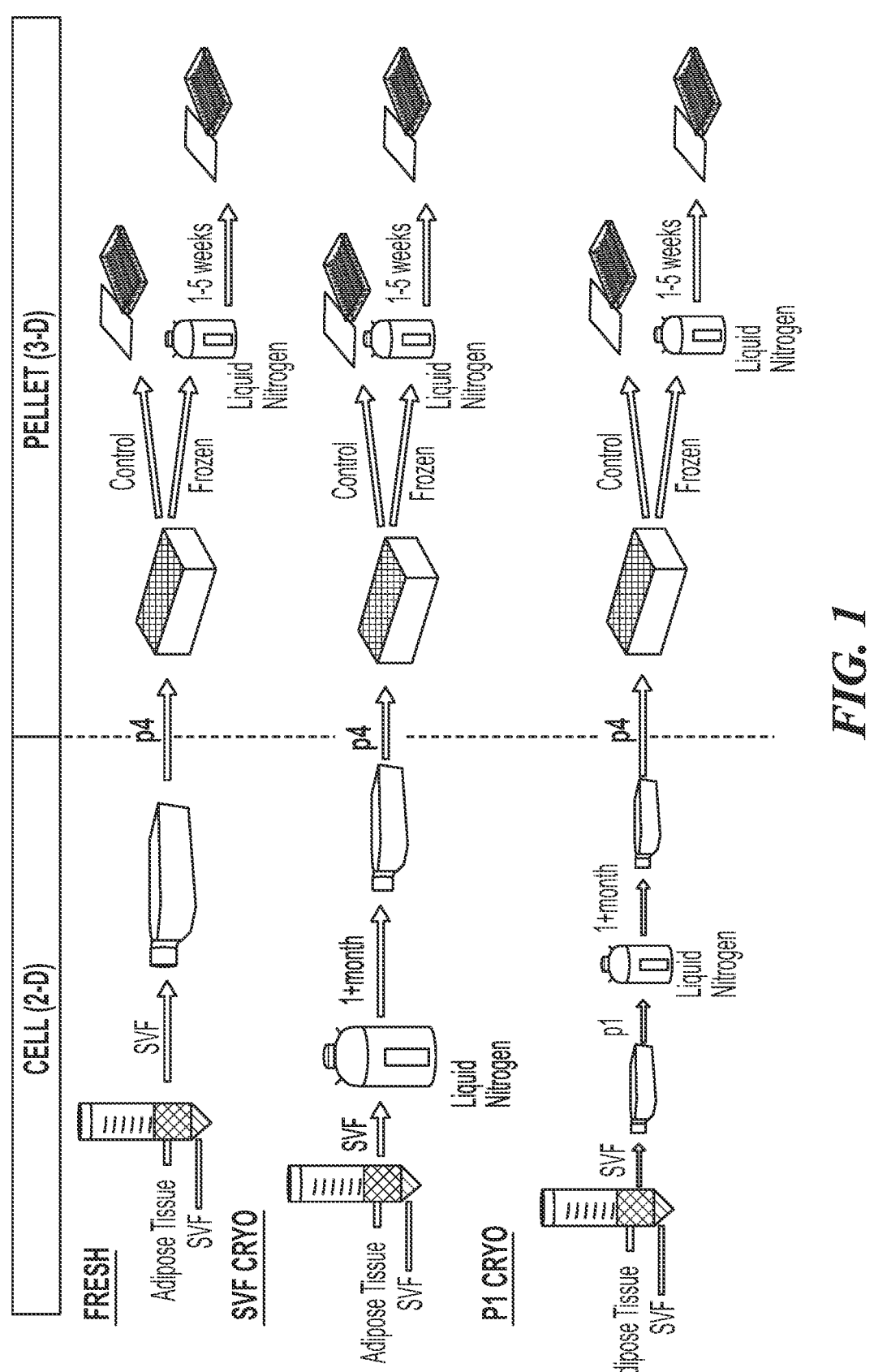
FIG. 1 shows a protocol for testing the effects of cryopreservation on ADSC-mediated chondrogenesis. To the left under "Cell (2-D)" is a schematic showing how ADSCs are treated before formation of CMBs. "Fresh" ADSCs do not undergo any cryopreservation, while "SVF Cryo" and "p1 Cryo" ADSCs under cryopreservation and storage in liquid nitrogen for at least one month. The "p1 Cryo" ADSCs undergo a single passage before cryopreservation while "SVF Cryo" ADSCs are not passaged before cryopreservation. To the right under "Pellet 3-D" is a description of formation of CMBs in multiwell plates, followed by another round of cryopreservation in the test samples. To form CMBs, the stromal vascular fraction (SVF) harvested from fresh human lipoaspirate is plated and passaged to P0 to P10 when ADSCs are harvested and re-suspended in chondrogenic media at 250,000 cells/mL. Subsequently, 1 mL of cell suspension is dispensed per well in a 96-well deep well plate and centrifuged for 5 minutes at 300 g. After centrifugation, the CMBs are maintained in chondrogenic medium.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

Definitions

It must be noted that, as used herein, the singular forms "a", "an" and "the" include plural references unless the context clearly dictates otherwise. For example, reference to a component is intended also to include composition of a plurality of components. References to a composition containing "a" constituent is intended to include other constituents in addition to the one named. In other words, the terms "a", "an" and "the" do not denote a limitation of quantity, but rather denote the presence of "at least one" of the referenced item. It is intended that each term contemplates its broadest meaning as understood by those skilled in the art and includes all technical equivalents which operate in a similar manner to accomplish a similar purpose.

Ranges may be expressed herein as from "about", "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within two-fold, of a value. Where particular values are described in the application and claims, unless otherwise stated, the term "about" is implicit and in this context means within an acceptable error range for the particular value.

By "comprising", "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

As used herein, and unless specified otherwise, the terms "hydrogel" and "scaffold," can mean but are in no way limited to, the hydrogel compositions taught and described herein, which comprise a network of polymers comprising an ionic, water-soluble polysaccharide, e.g., cellulose (e.g., NaCS or NaCP).

As used herein, the term "collagen," can mean but is in no way limited to, any of a family of extracellular, closely related proteins occurring as a major component of connective tissue, giving it strength and flexibility. At least 14 types exist, each composed of tropocollagen units that share a common triple-helical shape but that vary somewhat in composition between types, with the types being localized to different tissues, stages, or functions. In some types, including the most common, Type I, the tropocollagen rods associate to form fibrils or fibers; in other types the rods are not fibrillar but are associated with fibrillar collagens, while in others they form nonfibrillar, nonperiodic but structured networks. Cartilage can contain chondrocytes or chondrocyte-like cells and intracellular material, proteoglycans, and other proteins. Cartilage includes articular and non-articular cartilage.

"Articular cartilage," also referred to as hyaline cartilage, refers to an avascular, non-mineralized connective tissue, which covers the articulating surfaces of bones in joints and serves as a friction reducing interface between two opposing bone surfaces. Articular cartilage allows movement in joints without direct bone-to-bone contact. The cartilage surface appears smooth and pearly macroscopically, and is finely granular under high power magnification. Articular cartilage is associated with the presence of Type II and Type IX collagen and various well-characterized proteoglycans, and with the absence of Type X collagen, which is associated with endochondral bone formation.

"Non-articular cartilage" refers to cartilage that does not cover articulating surfaces and includes fibrocartilage (including interarticular fibrocartilage, fibrocartilaginous disc, connecting fibrocartilage and circumferential fibrocartilage) and elastic cartilage. In fibrocartilage, the micropolysaccharide network is interlaced with prominent collagen bundles, and the chondrocytes are more widely scattered than in hyaline or articular cartilage. Interarticular fibrocartilage is found in joints which are exposed to concussion and subject to frequent movement, e.g., the meniscus of the knee. Examples of such joints include but are not limited to the temporo-mandibular, sterno-clavicular, acromio-clavicular, wrist and knee joints. Secondary cartilaginous joints are formed by discs of fibrocartilage.

The term "cell" can mean, but is in no way limited to, its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "cellulose" can mean, but is in no way limited to, its usual biological sense. Cellulose is an organic compound with the formula $(C_6H_{10}O_5)_n$, a polysaccharide consisting of, e.g., a linear chain of several hundred to over ten thousand $\beta(1\rightarrow4)$ linked D-glucose units.

The term "defect" or "defect site", refers to a disruption of chondral, osteochondral tissue, meniscus, ligament, or tendon. A defect can assume the configuration of a "void", which is understood to mean a three-dimensional defect such as, for example, a gap, cavity, hole or other substantial disruption in the structural integrity of chondral and/or osteochondral tissue, meniscus, ligament, or tendon. A defect can also be a detachment of the cartilage from its point of attachment to the bone or ligaments. In certain embodiments, the defect is such that it is incapable of endogenous or spontaneous repair. A defect can be the result of accident, disease, and/or surgical manipulation. For example, cartilage defects may be the result of trauma to a joint such as a displacement of torn meniscus tissue into the joint. Cartilage defects can also arise from degenerative joint diseases such as osteoarthritis.

As used herein, the term "growth factor" can include a substance capable of stimulating cellular growth, proliferation, repair and cellular differentiation. The growth factor can be a drug. Drugs can include synthetic substances and naturally occurring substances. Growth factors include, but are not limited to, bone morphogenic proteins, fibroblast growth factors and vascular endothelial growth factors.

As used herein, the term "polymer," can mean but is in no way limited to, a macromolecule formed by the chemical union of five or more identical combining units called monomers. In most cases, the number of monomers is quite large and often is not precisely known. In synthetic polymers, this number may be controlled to a predetermined extent. Combinations of two, three, or four monomers are called, respectively, dimers, trimers, and tetramers, and are known collectively as oligomers. Polymers may be inorganic (e.g., siloxane, sulfur chains, black phosphorus, boron-nitrogen, silicones) or organic (meaning containing carbon).

As used herein, the term "homopolymer," can mean but is in no way limited to, a natural or synthetic polymer derived from a single monomer.

As used herein, the term "polysaccharide," can mean but is in no way limited to, a long-chain natural or synthetic polymer made up of linked simple sugars (monosaccharides) such as glucose and/or related molecules (e.g., glucuronate, galactose, galactosamine, glucosamine, acetyl glucosamine). Two monosaccharide molecules may be joined by a glycosidic bond to form a disaccharide, as, for instance, in the linkage of glucose and fructose to create sucrose. More complicated polysaccharides such as starch, glycogen, cellulose or chitin consist of numerous monosaccharide units joined by glycosidic bonds.

The term "repair" refers to new tissue formation which is sufficient to at least partially fill the void or structural discontinuity at the defect site and to any integration of newly formed tissues with native tissues such as articular cartilage, non-articular cartilage, ligament, and tendon surrounding the defect. Repair does not, however, mean, or otherwise necessitate, a process of complete healing, or a treatment which is 100% effective at restoring a defect to its pre-defect physiological/structural/mechanical state.

The term "therapeutically effective amount" refers to an amount effective to repair, regenerate, promote, accelerate, prevent degradation, or form cartilage tissue.

The term "patient" refers to an animal including a mammal (e.g., a human).

The term "pharmaceutically acceptable carrier" or "pharmaceutically acceptable adjuvant" refers to a non-toxic carrier or adjuvant that may be administered to a patient, together with a soluble morphogenic protein complex of this invention, which does not destroy the pharmacological activity thereof, and does not provoke an unacceptable immune response (e.g., a severe allergy or anaphylactic shock) based on the knowledge of a skilled practitioner. Examples include, but are not limited to, any of the standard pharmaceutical carriers such as carboxymethylcellulose (CMC), phosphate buffered saline solutions, water, emulsions such as oil/water emulsion, and various types of wetting agents. Exemplary diluents for aerosol or parenteral administration are phosphate buffered saline or normal (0.9%) saline.

As used herein, the term "stem cells," can mean but is in no way limited to, undifferentiated cells having high proliferative potential with the ability to self-renew that may migrate to areas of injury and may generate daughter cells that may undergo terminal differentiation into more than one distinct cell phenotype. These cells may be able to differentiate into various cells types and thus promote the regeneration or repair of a diseased or damaged tissue of interest. The term "cellular differentiation" refers to the process by which cells acquire a cell type. The term "progenitor cell" as used herein refers to an isolatable cell of any lineage that maintains the plasticity to differentiate into one or more target cell type that includes, but is not limited to, chondrocytes, osteocytes, and adipocytes. Progenitor cells are referred to as colony-forming units (CFU) or colony-forming cells (CFC). The specific lineage of a progenitor cell is indicated by a suffix, such as, but not limited to, CFU-F (fibroblastic). A progenitor cell, like a stem cell, may be able to differentiate into a specific type of cell, but is already more specific than a stem cell, and is pushed, or stimulated, to differentiate into its "target" cell. Generally, stem cells can replicate indefinitely, whereas progenitor cells can only divide a limited number of times.

As used herein, the terms "osteoprogenitor cells", "chondroprogenitor cells", "osteochondroprogenitor cells", "mesenchymal cells", "mesenchymal stem cells (MSC)", or "marrow stromal cells" are used interchangeably to refer to multipotent stem cells that differentiate from CFU-F cells capable of differentiating along one or several lineage pathways into osteoblasts, chondrocytes, myocytes, adipocytes, and tendocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium and surrounding environment.

As used herein, the term "chondrocytes" can mean but is in no way limited to, cells found in cartilage that produce and maintain the cartilaginous matrix. From least to terminally differentiated, the chondrocyte lineage is (i) a colony-forming unit-fibroblast (CFU-F); (ii) a mesenchymal stem cell/marrow stromal cell (MSC); or (iii) a chondrocyte. The term "chondrogenesis" refers to the formation of new cartilage from cartilage forming or chondrocompetent cells.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Examples of such carriers or diluents include, but are not limited to, water, saline, finger's solutions, dextrose solution, and 5% human serum albumin. Supplementary active compounds can also be incorporated into the compositions.

In one aspect is provided a composition comprising a condensed mesenchymal cell body (CMB) and a hydrogel. The composition may optionally comprise one or more growth factors.

In some embodiments, the CMB comprises mesenchymal stem cells (MSCs) such as adipose-derived stem cell (ADSC), bone marrow-derived stem cells (BMSCs), umbilical cord blood-derived mesenchymal stem cells (UM-MSCs), synovial-derived mesenchymal stem cells (SMSCs). Stem cells such as ADSCs offer a clinically relevant cell source for tissue engineering as they can be obtained from plentiful adipose tissue and expanded to large numbers without compromising the cell's ability for chondrogenic differentiation. Clinical-grade allogeneic BMSCs may be obtained from cryobanks and screened to select cells that exhibit the most robust levels of chondrogenesis. These MSCs may not be immunogenic or may have low immunogenicity. In addition to having the capacity for self-renewal and long-term growth, MSCs may be able to differentiate into diverse cell types, including adipocytes, osteoblasts, chondrocytes, hepatocytes, myocytes, cardiomyocytes, neurons, and epithelial cells.

MSCs may be isolated by a variety of methods known to those skilled in the art. See, e.g., U.S. Pat. No. 6,153,432. The adipose tissue used to prepare ADSCs may be derived from various adipose tissue sites, such as omental adipose tissue. Adipose tissue may be obtained or isolated by liposuction, with exemplary amounts isolated ranging from 10 to 300 mL. Bone marrow tissue used to prepare BMSCs may be derived from various bone marrow tissue sites, such as iliac crest. Bone marrow tissues may be obtained by needle aspiration, with exemplary amounts isolated in the range of about 20 mL per kg of donor's body weight.

MSCs can be engineered to contain genes that express growth factors, hormones, and cytokines. For example, the ADSCs can be engineered to express beneficial genes, cytokines or growth factors. For example, ADSCs which have been genetically modified to express anti-inflammatory cytokines (e.g., IL-2) can be transplanted into a location where inflammation is occurring (e.g., arthritic joint). The transplantation then provides a dual benefit to the subject because the ADSC can become a chondrocyte in addition to expressing beneficial, anti-inflammatory cytokines.

MSC-comprising compositions may be used to treat patients for osteoarthritis (OA). OA is characterized by degeneration of the articular cartilage, loss of matrix, fibrillation, and formation of fissures. OA can result in complete loss of the cartilage surface. Chondrocytes, the only cells of articular cartilage, maintain homeostatic synthesis and degradation of the extracellular matrix via the secretion of macromolecular components (collagen, glycosaminoglycans, and hyaluronic acid) and modulation of the extracellular matrix turnover. In OA, destructive and proinflammatory mediators are overproduced relative to the anabolic and reparative substances, resulting in the progressive destruction of articular cartilage.

The MSC may be anti-immunogenic. In some embodiments, the MSC is from an allogenic source.

Allogenic cells may provide several advantages. Since allogenic cells can be isolated from readily available donor tissues, off-the-shelf compositions can be produced. Testing and comparing the chondrogenic potential across several donor cell lots can improve the quality of any final products. Cells from a universal donor would reduce costs and variability since large cell numbers and several products can be produced from a single batch [20].

Expanded undifferentiated MSCs may not express MHC Class II molecules. Chondrogenic-induced MSCs (such as by application of growth factors TGF-β3 and BMP-6) may also not express MHC Class II molecules. MSCs from an allogenic source, such as those that do not express MHC Class II molecules, can be implanted into a donor without induction of an immune response. Various animal studies may be performed to confirm that the implanted ADSCs do not induce an immune response.

In some embodiments, the composition, the CMBs and the MSCs do not express a substantial or detectable amount of human leukocyte antigen (HLA) class II, CD40, CD80, or CD86 on the cell surface according to a flow cytometry and mixed lymphocyte reaction assays. Cells lacking expression of HLA class II, CD40, CD80, and CD86 may be considered immunoprivileged.

To detect these markers, thawed CMBs may be dissociated into single cell suspensions by incubating in type I collagenase for 1 hour at 37° C. [21]. Digests would then be neutralized with approximately equal volumes of chondrogenic medium and cell suspensions, and dissociated further by resuspending through a 20G needle. Single cells can be stained with surface marker-specific antibodies and Calcein AM following the manufacturer's protocol for flow cytometry. Flow cytometry may then be conducted using Flow Cytometer.

In some embodiments, the CMBs are hypothermically preserved. In some embodiments, the CMBs are hypothermically preserved at room temperature or at a temperature of from 0° C. to 10° C. In some embodiments, the CMBs are cryopreserved, e.g., at a temperature of about −20° C., at a temperature of about −80° C. or at a temperature of less than about −80° C. In various embodiments, the CMBs are hypothermically preserved or cryopreserved for at least about one week. The CMBs that are hypothermically preserved or cryopreserved may exhibit similar performance characteristics as comparable "fresh CMBs" that were not hypothermically preserved or cryopreserved. The hypothermically preserved or cryopreserved CMBs may exhibit cell viability (which may be tested by a LIVE/DEAD assay using, for example, ORFLO MoxiFlo and Moxi GO II) comparable to that of fresh CMBs, or non-hypothermically preserved or cryopreserved CMBs. Hypothermic preservation or cryopreservation may be undertaken by introducing CMBs into a medium comprising a stabilizer such as DMSO (for example, Synth-a-Freeze® from Gibco). Hypothermic preservation or cryopreservation of the CMBs and the compositions comprising CMBs may be optimized to improve characteristics for long-term storage and off-the-shelf usage.

Various tests can be performed on hypothermically preserved or cryopreserved CMBs. The hypothermically preserved or cryopreserved CMBs may be cultured in chondrogenic medium (for example, StemPro SFM media (Life Technologies) supplemented with ascorbic acid, dexamethasone, ITS+ Premix (Corning), MSC supplement, TGF-β3 (R&D Systems), and BMP6 (R&D Systems) to assess for the maintenance of chondrogenic quality. Cultured CMBs may then be fixed in 10% (vol/vol) formalin for histological and immunohistochemical analysis or stored in TRI reagent for gene expression analysis. After fixation, samples are paraffin-embedded, cut into 5 μm sections and stained with hematoxylin and eosin (H&E), Alcian blue for GAG, trichrome, collagens I, II, X, and lubricin (Abcam). RNA may be purified from the samples according to the manufacturer's instructions using the TRI reagent method (Life Technologies).

Expression of one or more of the following genes may be evaluated: aggrecan (ACAN), collagen type I (COL1A1), type II (COL2A1), type X (COL10A1), sex determining region Y (SRY)-box 9 (SOX9) and homeobox A2 (HOXA2) mesenchymal condensation transcriptional factors, cell adhesion cadherin 2 (CDH2), condensation extracellular matrix fibronectin (FN1), tenascin C (TNC), syndecan 3 (SDC3), matrix metalloproteinase 13 (MMP13), a disintegrin and metalloproteinase with thrombospondin motifs-5 (ADAMTS5), transforming growth factor beta (TGF-β1 and TGF-β3), and bone morphogenetic protein 6 (BMP6). Real-time PCR using TaqMan primers (Life Technologies) may be undertaken for the gene expression analysis. Comparison of the expression of any of the above genes between fresh and hypothermically preserved CMBs may be undertaken, with a housekeeping gene which includes, but is not limited to, glyceraldehyde-3-phosphate dehydrogenase (GAPDH), S18, L37, EF1, EF2, and actin.

The CMB is a precursor cellular structure for cartilage formation. A CMB may be prepared by culturing human MSCs, such as ADSC, and allowing them to form an aggregate. The CMB may form, for example, after any of one day, two days, three days, four days, five days, six days, seven days, eight days or even nine days of culturing. CMBs that have cultured for at least six days may form a border or boundary and thus be "mature CMB." CMBs may express one or more of the following markers indicating that they are "mature CMBs" or CMBs that is cartilage-specific: aggrecan (ACAN), collagen type I (COL1A1), collagen type II (COL2A1), collagen type X (COL10A1), mesenchymal condensation transcriptional factors sex determining region Y (SRY)-box 9 (SOX9), homeobox A2 (HOXA2), cell adhesion cadherin 2 (CDH2), condensation extracellular matrix fibronectin (FN1), tenascin C (TNC), syndecan 3 (SDC3), matrix metalloproteinase 13 (MMP13), a disintegrin and metalloproteinase with thrombospondin motifs-5 (ADAMTS5), transforming growth factor beta (TGF-β1 and TGF-β3), and bone morphogenetic protein 6 (BMP6). Fusion of immature CMB may be effective to repair existing cartilage, such as when present in the composition comprising CMB, the hydrogel and one or more growth factors.

The hydrogel may be comprised of a polymer network or scaffold that may mimic the natural gel-like medium of the extracellular matrix. In certain embodiments, the natural gel-like medium is collagen or fragmented collagen or gelatin. In certain embodiments, the natural gel-like medium is hyaluronic acid or modified hyaluronic acid. The hydrogel can comprise a network of polymers or microfibrils comprising a hydrophilic or water-soluble polysaccharide compound. In certain embodiments, the soluble polysaccharide compound is a water-soluble cellulose compound. In certain embodiments, the water-soluble cellulose compound is an anionic, water-soluble cellulose.

The hydrogel or scaffold may further comprise a matrix or mesh of substantially insoluble fibers or filaments. (The terms "hydrogel" and "scaffold" are used interchangeably herein.) In certain embodiments, the hydrogel comprises a polymeric network of an ionic, water-soluble cellulose compound, and a polyionic polysaccharide, e.g., a polycationic polysaccharide, e.g., chitosan, in an amount sufficient to form a fibrous or filamentous mesh or matrix within the hydrogel. In certain embodiments, the polycationic polysaccharide is chitosan. In additional embodiments, the effective amount of chitosan included ranges from about 0.01% to about 20% (w/w) with respect to the weight of the hydrogel.

The hydrogels or scaffolds may further comprise a complexing or stabilizing agent, for example, a counter-ion (anion or cation) or chemical cross-linker. The complexing or stabilizing agent confers additional biochemical and/or biomechanical stability or both to the hydrogel by interacting or complexing with the cellulose polymers, e.g., via hydrophobic, covalent, ionic, hydrogen, van der Waals forces or other chemical bond. In certain embodiments, the hydrogel or scaffold comprises an anionic cellulose compound and a cation. In certain embodiments, the cation comprises a divalent cation, such as, e.g., calcium, magnesium, manganese, or iron(II). Various bioresorbable polymers, scaffolds, and components thereof may be used as described in International Application No. PCT/US2017/019956, published as WO2017/151619 on Sep. 8, 2017.

In additional embodiments, the hydrogel or scaffold comprises an ionic, water-soluble cellulose compound and a chemical cross-linking agent. A wide variety of suitable chemical cross-linking agents are known in the art. For example, suitable cross-linking for use in the hydrogels described herein include those that react with, e.g., amines, sulfate groups, hydroxyl groups, thiol groups, diacrylates, glycosidic bonds, such as, e.g., polydiallyl dimethyl ammonium chloride (PDADMAC) and bisepoxides. In certain embodiments the cross-linking agent is a diglycidyl ether, e.g., diisosorbide bisepoxide.

In some embodiments, the hydrogel comprises glycosaminoglycans (GAGs). In the body, adult stem cells are often localized to specific chemically and topologically complex microenvironments, or niches. Mimicking characteristics of the microenvironment during cartilage development may be a viable approach. During cartilage development, one of the earliest events is pre-cartilage mesenchymal cell aggregation and condensation resulting from cell-cell interaction, which is mediated by both cell-cell and cell-matrix adhesion. GAGs are present during cartilage development, particularly chondroitin-4-sulfate, chondroitin-6-sulfate and heparin sulfate. Growth factors can bind to these GAGs.

In various embodiments, the hydrogel may comprise between about 1.0% to about 95% of the mass of the composition. In some embodiments, the composition comprises from 1.0 to 3.0% hydrogel, from 2.0 to 4.0% hydrogel, from 3.0 to 6.0% hydrogel, from 4.0 to 8.0% hydrogel, from 5.0 to 10.0% hydrogel, from 7.0 to 12.0% hydrogel, from 10.0 to 15.0% hydrogel, from 15 to 25% hydrogel, from 20 to 30% hydrogel, from 25 to 40% hydrogel, from 30 to 45% hydrogel, from 35 to 50% hydrogel, from 40 to 55% hydrogel, or from 50 to 70% hydrogel.

The hydrogel may be supported by a nano-fibrous network or framework composed of protein filaments to which cells can attach. Soluble nutrients can diffuse through the hydrogel. In the natural ECM, the hydrogel mediates compressive stress. Water is strongly absorbed by GAGs, which allows GAGs to provide cartilage its resistance to pressure. Hydrogel consistency is maintained by proteoglycans, which are composed of GAGs. Also, the GAGs sequester growth factors. GAGs vary in the type of hexosamine, hexose or hexuronic acid unit they contain (e.g., glucuronic acid, iduronic acid, galactose, galactosamine, glucosamine). The specific GAGs of physiological significance are hyaluronic acid, dermatan sulfate, chondroitin sulfate, heparin, heparan sulfate, and keratan sulfate.

The hydrogel or scaffold may comprise at least two materials. In certain embodiments, the materials are polysaccharides, such as, e.g., two water-soluble cellulose compounds. In certain embodiments, the materials are collagen or collagen based matrices. In certain embodiments, the materials comprise collagen and hyaluronic acid. In certain embodiments, the compounds are cross-linked as described herein, e.g., by means of ionic or chemical interactions.

Growth factors include naturally occurring substances capable of stimulating cellular growth, proliferation, repair and cellular differentiation. Usually, the growth factor is a protein or small molecule, e.g., a steroid hormone, which binds to specific receptors in/on the target cells. Growth factors are important for regulating a variety of cellular processes and typically act as signaling molecules between cells. Growth factors include, for example, bone morphogenic proteins, while fibroblast growth factors and vascular endothelial growth factors stimulate blood vessel differentiation (angiogenesis).

Exemplary growth factors that can be used in any of the embodiments taught and described herein include, but are not limited to: autocrine motility factor, bone morphogenetic proteins (BMPs), epidermal growth factor (EGF), erythropoietin (EPO), fibroblast growth factor (FGF), granulocyte-colony stimulating factor (G-CSF), granulocyte-macrophage colony stimulating factor (GM-CSF), growth differentiation factor-9 (GDF9), hepatocyte growth factor (HGF), hepatoma derived growth factor (HDGF), insulin-like growth factor (IGF), migration-stimulating factor, myostatin (GDF-8), nerve growth factor (NGF), brain-derived neurotrophic factor (BDNF) and other neurotrophins, platelet-derived growth factor (PDGF), thrombopoietin (TPO), transforming growth factor alpha (TGF-α), transforming growth factor beta (TGF-β), vascular endothelial growth factor (VEGF), placental growth factor (PLGF), and/or fetal bovine somatotrophin (FBS).

In some embodiments, the growth factor is a morphogenic protein. Morphogenetic proteins include members of the bone morphogenetic protein (BMP) family, particularly BMP-6. The members of this family are a subclass of the TGF-β super-family of proteins. Exemplary morphogenic proteins that may be used as growth factors include OP-1, OP-2, OP-3, BMP-2, BMP-3, BMP-4, BMP-5, BMP-6, BMP-8, BMP-9, BMP-10, BMP-11, BMP-12, BMP-13, BMP-15, BMP-16, BMP-17, BMP-18, DPP, Vg1, Vgr-1, 60A protein, GDF-1, GDF-2, GDF-3, GDF-5, GDF-6, GDF-7, GDF-8, GDF-9, GDF-10, GDF-11, GDF-12, CDMP-1, CDMP-2, CDMP-3, NODAL, UNIVIN, SCREW, ADMP, and NEURAL.

The growth factor (or drug) can induce differentiation of the ADSCs in the CMB into chondrocytes in situ. In some embodiments, the growth factor is TGF-β3, BMP-6, or a combination of TGF-β3 and BMP-6. If TGF-β3 and BMP-6 are combined, they may be present in a mass ratio (TGF-β3 to BMP-6) of 1:5, 1:4, 1:3, 1:2.5, 1:2, 1:1.5, 1:1.25, 1:1, 1.25:1, 1.5:1, 2:1, 2.5:1, 3:1, 4:1, 5:1, or from 1:5 to 1:3, 1:4 to 1:2.5, 1:3 to 1:2, 1:2.5 to 1:1.5, 1:2 to 1:1.25, 1:1.5 to 1:1, 1:1.25 to 1.25:1, 1:1 to 1.5:1, 1.25:1 to 2:1, 1.5:1 to 2.5:1, 2:1 to 3:1, 2.5:1 to 4:1, or 3:1 to 5:1. If microspheres are present in the composition, and TGF-β3 and BMP-6 are combined, they may be present in a mass ratio (TGF-β3 to BMP-6) of 1:5, 1:4, 1:3, 1:2.5, 1:2, 1:1.5, 1:1.25, 1:1, 1.25:1, 1.5:1, 2:1, 2.5:1, 3:1, 4:1, 5:1, or from 1:5 to 1:3, 1:4 to 1:2.5, 1:3 to 1:2, 1:2.5 to 1:1.5, 1:2 to 1:1.25, 1:1.5 to 1:1, 1:1.25 to 1.25:1, 1:1 to 1.5:1, 1.25:1 to 2:1, 1.5:1 to 2.5:1, 2:1 to 3:1, 2.5:1 to 4:1, or 3:1 to 5:1.

In one embodiment, TGF-β3 may be included in the hydrogel or scaffold matrix. TGF-β3 may be detected during chondrogenesis during development in vivo. Such immobilization may be detected using previously reported protocols. For example, various concentrations of TGF-β3 in BSA-PBS are added to cross-linked NaCS films overnight at 4° C. Wells are washed with BSA-PBS and immunofluorescent staining is performed using mouse anti-human TGF-β3 (Abeam, Inc.) followed by secondary, anti-mouse IgG conjugated with FITC (BD Biosciences, Inc). Fluorescent intensity is then detected using a fluorescent plate reader (FLX800, Biotek, Inc.) and correlated with the amount of TGF-β3.

In various embodiments, the growth factor may comprise between about 10 to about 10000 ng per cc of the composition. In some embodiments, the composition comprises from 1-15 ng growth factor, from 10 to 100 ng growth factor, from 20 to 200 ng growth factor, from 50 to 500 ng growth factor, from 100 to 1000 ng growth factor, from 200 to 2000 ng growth factor, from 500 to 3000 ng growth factor, from 1000 to 4000 ng growth factor, from 2000 to 5000 ng growth factor, from 3000 to 6000 ng growth factor, from 4000 to 7000 ng growth factor, or from 5000 to 8000 ng growth factor, from 6000 to 10000 ng growth factor per cc of the composition.

Growth factors present in the composition can provide for differentiation of CMBs into chondrocytes in the joint or other site where the composition is injected. Growth factors present in the composition can signal CMBs to produce glycosaminoglycan (GAG) or collagen or hyaluronic acid. Growth factors present in the composition, along with hydrogel and CMBs, can advantageously provide for physiologic developmental processes of mesenchymal condensation which, after implantation, potentially forms cartilage and integrates with adjacent tissue. The amount and release rate of the growth factors can be optimized to provide for such developmental processes. Use of materials to sequester and slowly release growth factors can provided for extended exposure of the CMBs to growth factor during the developmental process.

In some embodiments, the composition further comprises a polymer microsphere, wherein one or more of the growth factors is encapsulated in the polymer microsphere. In some embodiments, the polymer microsphere comprises poly(lactic-co-glycolic acid) (PLGA). The polymer microsphere may provide for controlled release of the growth factors so that such growth factors are effective to induce chondrogenic differentiation of the MSCs in situ over several days or weeks. Without wishing to be bound by theory, hydrogels comprising polymer microspheres, such as PLGA, may provide for superior long-term growth factor release than hydrogels alone. PLGA-based microspheres may sustain controlled-release of a growth factor, such as VEGF, BMP6 and TGF-β3, for as long as 90 days. Such controlled release in a substantially constant manner can allow for formation of a dense and functional cell layer for osteochondral repair.

In addition, PLGA and other polymer microspheres are lyophilizable and storable, which can allow for the composition to be used off-the-shelf.

In some embodiments, the composition further comprises a stabilizer, such as fibrin, laminin, poly-D-lysine and/or poly-L-lysine. As fibrin is formed from thrombin and fibrinogen, these components may be present separately and later combined. For example, the thrombin and fibrinogen could be combined shortly before the composition is injected into a joint or other site where cartilage repair is needed. Laminin (LN) is an adhesive glycoprotein of high molecular weight. Poly-D-lysine and poly-L-lysine may be advantageous because they can be prepared from a nonbiological source. The amounts of the stabilizer can be varied such that the composition has a gel-like consistency suitable for holding the CMBs, hydrogel and growth factors at a site of injection.

In various embodiments, the composition is prepared by mixing the CMB and the hydrogel. One or more drugs may be added to the composition. One or more growth factors may be added to the composition. The composition comprising the CMB and the hydrogel may be cryopreserved and stored in liquid nitrogen for at least 5 days, 10 days, 15 days, 20 days, 25 days, 30 days, 2 months, 3 months, 4 months, 6 months, one year, three years, five years, or even ten years. During preparation, the composition may also be subjected to mixing under a mechanical load. The mechanical load may be applied manually, by agitation, by dynamic loading or by hydrostatic pressure, for example.

In various embodiments, when administered to a subject or patient, the hydrogel or scaffold is effective for supporting, promoting, and/or enhancing the growth, regeneration, and/or repair of the tissue.

The compositions described herein can be administered together with a pharmaceutically acceptable carrier, excipient, and/or an adjuvant. The composition may be combined with at least one additional biologically active and/or therapeutic agent, such as an amino acid, peptide, polypeptide, chemical compound, drug, antibody or the like, or a combination thereof. For example, the hydrogel or scaffold composition may comprise at least one additional biologically active and/or therapeutic agent such as an amino acid, peptide, polypeptide, chemical compound, drug, antibody or the like, or a combination thereof.

Aqueous suspensions may contain active materials in admixture with excipients suitable for the manufacture of aqueous suspensions. Such excipients include suspending agents, for example sodium carboxymethylcellulose, methylcellulose, hydropropyl-methylcellulose, sodium alginate, polyvinylpyrrolidone, gum tragacanth and gum acacia. Exemplary excipients also include dispersing or wetting agents, for example, lecithin, or condensation products of an alkylene oxide with fatty acids, for example polyoxyethylene stearate. Exemplary excipients also include condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

Aqueous suspensions can also contain one or more preservatives, for example ethyl, or n-propyl p-hydroxybenzoate, one or more coloring agents, one or more flavoring agents, and one or more sweetening agents, such as sucrose or saccharin.

Pharmaceutical compositions suitable for injectable use may include sterile aqueous solutions (where water-soluble) or dispersions and sterile powders for the extemporaneous preparation of sterile injectable solutions or dispersion. Formulations for injection may be presented in unit dosage form, e.g., in ampoules or in multi-dose containers, with an added preservative. The compositions may be formed as suspensions, solutions, or emulsions in oily or aqueous vehicles, and may contain suspending, stabilizing, and/or dispersing agents.

For intravenous administration, suitable carriers include physiological saline, bacteriostatic water, Cremophor™. (BASF, Parsippany, N.J.) or phosphate buffered saline (PBS). The composition may be sterile and fluid to the extent that easy syringeability exists. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as mannitol, sorbitol, and sodium chloride, may be included in the composition. Prolonged absorption of the injectable compositions can be brought about by including in the composition an agent which delays absorption, for example, aluminum monostearate and gelatin.

A bioreactor may be used to prepare the composition, with exemplary bioreactors described in as described in International Application No. PCT/US10/026120, published as WO 2010/102059 on Sep. 10, 2010 and in International Application No. PCT/US14/034559, published as WO 2014/172575 on Oct. 23, 2014. During manufacturing, allogeneic donor cells may be used to generate CMBs, which are then hypothermically preserved or cryopreserved at the optimal time point for implantation. Similarly, growth factor-infused microparticles may be produced and lyophilized so that they are readily available for shipment with CMBs created from large allogeneic pools of donor cells to allow for off-the-shelf use.

In various embodiments, the compositions, or any components thereof, may be tested in vitro before administration to a patient or as part of a quality control procedure. The compositions may have been hypothermically preserved or cryopreserved before testing. One manner of testing is to assay the chondrogenic properties of the composition or the CMBs therein. The CMBs of the composition may be thawed, if applicable, and then cultured in a chondrogenic medium. For example, after thawing, the CMBs may be cultured in chondrogenic differentiation media (CDM) for one or more days and then combined with a hydrogel before implantation. Assays of one or more of cell viability, histology, and gene expression may be undertaken. Specific assays are described in Example 1. For example, cultured CMBs may be fixed and stained. Various stains may be used in histological analysis, such as hematoxylin, eosin, Alcian blue, and trichrome. For gene expression, real time PCR may be undertaken to evaluate expression of aggrecans, collagens, SOX9, HOXA2, cadherin 2, fibronectin, tenascin C, syndecan 3, matrix metalloproteinases (MMPs), a disintegrin and metalloproteinase with thrombospondin motifs (ADAMTSs), transforming growth factor betas, and bone morphogenetic proteins. Such testing may be undertaken to optimize or improve the manner of formulating, hypothermically preserving or cryopreserving, and/or storing the compositions.

The compositions may be tested for immunogenicity. Markers of immunogenicity on the MSCs that are present in the CMBs may be tested, such as by flow cytometry. Exemplary markers include, but are not limited to, human leukocyte antigen (HLA) class II, CD40, CD80, and CD86. An example of such testing is described in Example 1.

The compositions may be tested for efficacy in repairing a cartilage defect in vivo. Cartilage defects may be created, either in an animal-based cartilage explant or simulated by using an artificial material, such as a silicone rubber ring. Alternatively, connective tissue defects may be created. The composition is then pressed into the defect and cultured in a chondrogenic medium. Optionally, mechanical force is provided to the composition to promote development of cartilage cells or to otherwise simulate conditions in vivo, such as in the knee or shoulder. The composition may later be tested to determine the mechanical strength (by measuring compressive Young's modulus). Further, if mechanical force is provided, such as by dynamic loading, histology studies described above and in Example 2 may be conducted to assess the effect of mechanical force on development of cartilage cells.

In another aspect is provided a method of treating a cartilage defect in a patient comprising administering any of the compositions described above and herein into the cartilage or into the area surrounding the cartilage. The composition may be injected into the defect site. For example, the composition may be injected into the meniscus of the knee. Alternatively, the cartilage may be injected at a site near the meniscus of the knee. Also, the composition may be injected into the synovial fluid or be in contact with synovial fluid.

In another aspect is provided a method of preventing cartilage degradation or treating cartilage injury or degenerative disease or disorder in a patient comprising administering any of the compositions described above and herein into the cartilage or into the area surrounding the cartilage. The composition may be implanted and fixed into a cartilage lesion or defect. Because cartilage lesions and defects can occur in a variety of shapes, sizes, and locations, the composition may be molded into a shape and size sufficient to conform to the specific cartilage defect or lesion in the cartilage of the patient to be treated. For example, the composition may be molded as a sheet or matrix. The sheet or matrix may have a thickness of 0.5 to 10 mm, 1 to 1.5 mm, 1.5 to 3 mm, 2.5 to 4 mm, 3.5 to 5 mm, 4 to 6 mm, 5 to 7 mm, 6 to 8 mm, or 8 to 10 mm. The thickness can vary throughout the sheet or matrix. Additional matrices, meshes, and other components may be used as needed to secure the implant into the cartilage defect.

In another aspect is provided a method of preventing connective tissue degradation or treating connective tissue injury or degenerative disease or disorder in a patient comprising administering any of the compositions described above and herein into the connective tissue or into the area surrounding the connective tissue. The composition may be implanted and fixed into a connective tissue lesion or defect. Because connective tissue lesions and defects can occur in a variety of shapes, sizes, and locations, the composition may be molded into a shape and size sufficient to conform to the specific connective tissue defect or lesion in the connective tissue of the patient to be treated. For example, the composition may be molded as a sheet or matrix. The sheet or matrix may have a thickness of 0.5 to 10 mm, 1 to 1.5 mm, 1.5 to 3 mm, 2.5 to 4 mm, 3.5 to 5 mm, 4 to 6 mm, 5 to 7 mm, 6 to 8 mm, or 8 to 10 mm. The thickness can vary throughout the sheet or matrix. Additional matrices, meshes, and other components may be used as needed to secure the implant into the connective tissue defect.

In some embodiments of the above methods, the connective tissue is a meniscus, a ligament or a tendon. In some embodiments of the above methods, the cartilage is selected from articular and non-articular cartilage. In some embodiments, the non-articular cartilage is selected from the group consisting of a meniscus and an intervertebral disc. In some embodiments, the method is effective to form tissue comprising 1-20% (w/w) glycosaminoglycan (GAG) in the site of the connective tissue defect, cartilage defect, cartilage degradation, cartilage injury, cartilage degenerative disease or cartilage disorder. The tissue may comprise from 1.0 to 5.0% (w/w) GAG, 3.0 to 6.0% (w/w) GAG, 4.0 to 8.0% (w/w) GAG, 5.0 to 10.0% (w/w) GAG, 6.0 to 11.0% (w/w) GAG, 7.0 to 12.0% (w/w) GAG, 8.0 to 13.0% (w/w) GAG, 9.0 to 14.0% (w/w) GAG, 10.0 to 15.0% (w/w) GAG, 11.0 to 16.0% (w/w) GAG, 12.0 to 17.0% (w/w) GAG, 13.0 to 18.0% (w/w) GAG, 14.0 to 19.0% (w/w) GAG, or 15.0 to 20.0% (w/w) GAG. In some embodiments, the method is effective to form tissue comprising 0.5-20% (w/w) collagen in the site of the connective tissue defect, cartilage defect, cartilage degradation, cartilage injury, cartilage degenerative disease or cartilage disorder. The tissue may comprise from 0.5 to 5.0% (w/w) collagen, 1.0 to 5.0% (w/w) collagen, 2.0 to 7.0% (w/w) collagen, 3.0 to 8.0% (w/w) collagen, 4.0 to 9.0% (w/w) collagen, 5.0 to 10.0% (w/w) collagen, 6.0 to 11.0% (w/w) collagen, 7.0 to 12.0% (w/w) collagen, 8.0 to 13.0% (w/w) collagen, 9.0 to 14.0% (w/w) collagen, 10.0 to 15.0% (w/w) collagen, 10.0 to 15.0% (w/w) collagen, 12.0 to 17.0% (w/w) collagen, 14.0 to 19.0% (w/w) collagen, or 15.0 to 20.0% (w/w) collagen. The tissue may comprise at least 1.2% (w/w), 1.3% (w/w), 1.4% (w/w), or 1.6% (w/w) collagen. In some embodiments, the method is effective to form tissue comprising at least 1% (w/w) GAG in the site of the cartilage defect, cartilage degradation, cartilage injury, cartilage degenerative disease or cartilage disorder. In some embodiments, the method is effective to form cartilage having a Young's modulus of at least 100 kPa and a friction coefficient of at most 0.8 in the site of the cartilage defect, cartilage degradation, cartilage injury, cartilage degenerative disease or cartilage disorder. The Young's modulus may be at least 20 kPa, 25 kPa, 30 kPa, 40 kPa, 50 kPa, 75 kPa, 100 kPa, 125 kPa, 150 kPa, 175 kPa, 200 kPa, at least 300 kPa, at least 400 kPa, at least 500 kPa, at least 600 kPa, at least 700 kPa, at least 800 kPa, at least 900 kPa, at least 950 kPa, at least 1000 kPa, at least 1100 kPa, at least 1200 kPa, or at least 1300 kPa. The friction coefficient may be below 0.8, 0.75, 0.7, 0.65, 0.6, 0.55, 0.5, 0.49, 0.48, 0.47, 0.46, 0.45, 0.44, 0.43, 0.42, 0.41, 0.40, 0.39, 0.38, 0.37, 0.36, 0.35, 0.34, 0.33, 0.32, 0.31, 0.30, 0.29, 0.28, 0.27, 0.26, 0.25, 0.24, or 0.23.

In some embodiments, the method is effective to form cartilage in the site of the cartilage defect, cartilage degradation, cartilage injury, cartilage degenerative disease or cartilage disorder. In some embodiments, the cartilage is integrated with any adjacent cartilage and subchondral bone tissue at or surrounding the site.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Demonstrate Chondrogenic Properties of Cryopreserved Allogeneic CMBs Early passage, expanded adipose-derived stem cells (ADSCs) are obtained from LaCell LLC and thoroughly tested for antigenicity. The cells are expanded and passaged using GMP-grade components. After the fourth passage, the ADSCs are introduced into chondrogenic medium, where CMBs are formed.

Once CMBs have formed, they are immediately cryopreserved in Synth-a-freeze (Gibco) by lowering the temperature to −80° C. at a rate of −1° C./minute, followed by transfer to liquid nitrogen after at least 3 days at −80° C. After one to five weeks of cryopreservation, frozen CMBs are thawed by quickly rewarming to 37° C. in a 37° C. water bath. Cell viability is measured using the LIVE/DEAD Viability/Cytotoxicity Assay kit (Invitrogen) or trypan blue exclusion. Immunohistochemical and gene expression analyses are performed on thawed CMBs, by comparing the results obtained on the thawed CMBs with CMBs that were not cryopreserved.

Furthermore, the cryopreserved CMBs are cultured in a chondrogenic medium, i.e., StemPro SFM media (Life Technologies) supplemented with ascorbic acid, dexamethasone, ITS+ Premix (Corning), MSC supplement, TGFβ3 (R&D Systems), and BMP6 (R&D Systems) to assess for the maintenance of chondrogenic quality. Briefly, cultured CMBs are fixed in 10% (vol/vol) formalin for histological and immunohistochemical analysis or stored in TRIzol for gene expression analysis. After fixation, samples are paraffin-embedded, cut into 5 μm sections and stained with hematoxylin and eosin (H&E), Alcian blue for GAG, trichrome, mesenchymal condensation transcriptional factors sex determining region Y (SRY)-box 9 (SOX9), collagens I, II, X, and lubricin (Abcam). RNA is purified from the samples according to manufacturer's instructions using the TRIzol method (Life Technologies). Realtime PCR is performed using TaqMan primers (Life Technologies) to evaluate expression of the following genes: aggrecan (ACAN), collagen type I (COL1A1), type II (COL2A1), type X (COL10A1), mesenchymal condensation transcriptional factors sex determining region Y (SRY)-box 9 (SOX9) and homeobox A2 (HOXA2), cell adhesion cadherin 2 (CDH2), condensation extracellular matrix fibronectin (FN1), tenascin C (TNC), syndecan 3 (SDC3), matrix metalloproteinase 13 (MMP13), a disintegrin and metalloproteinase with thrombospondin motifs-5 (ADAMTS5), transforming growth factor beta (TGFβ1 and TGFβ3), and bone morphogenetic protein 6 (BMP6). Glyceraldehyde-3-phosphate dehydrogenase (GAPDH) is used as the housekeeping gene.

To better understand the antigenicity of allogeneic ADSCs after CMB formation, cryopreserved samples are analyzed by flow cytometry to detect human leukocyte antigen (HLA) class II, CD40, CD80, and CD86 surface marker levels. Cells lacking expression of the aforementioned markers are considered to be immunoprivileged [22]. Briefly, thawed CMBs are dissociated into single cell suspensions by incubating the CMBs in type I collagenase for 1 hour at 37° C. to break up any pellets. Digests are neutralized with an equal volume of chondrogenic medium. Cell suspensions are dissociated further by resuspending through a 20G needle. Single cells are stained with surface marker-specific antibodies and Calcein AM following the manufacturer's protocol for On-Chip Staining (Agilent). Flow cytometry is conducted using the Agilent Bioanalyzer, Guava® easyCyte Flow Cytometers, or another flow cytometer.

Methods of producing the CMBs are optimized as needed to achieve (i) comparable performance of cryopreserved/thawed CMBs vs fresh products, (ii) homogenous integration and fusion of ADSCs into mesenchymal bodies (homogenous glycosaminoglycan structure, low tenascin deposition), and (iii) absence of immunogenic surface markers on cells after CMB formation.

Example 2: In Vitro Model of Administered Allogeneic CMBs in Hydrogel

The feasibility and efficacy of CMBs/hydrogel in filling an in vitro cartilage defect model is tested using cryopreserved and freshly-formed CMBs. In nonviable bovine cartilage explants (5 mm diameter and 5 mm height), a 3 mm diameter full-thickness cartilage defect is created. CMBs are inserted into the defects with various hydrogel vehicles. Each vehicle comprises one or more of type I collagen, hyaluronic acid, and fibrin, with comparative analysis of the vehicles undertaken to determine the optimal hydrogel composition. The hydrogel vehicles are then pressed into the defects (FIG. 4). The constructs are cultured for up to 5 weeks in chondrogenic medium containing TGF-β3 and BMP-6, as defined above, and analyzed. Histological, biochemical, and mechanical analyses are performed [19]. DNA, GAG, and hydroxyproline (collagen) contents are also measured.

Briefly, the cartilage and subchondral regions are separated along the surface of the underlying bone and the wet weights are determined. The samples are digested and DNA content determined using the PicoGreen Assay (Molecular Probes). The sulfated GAG (s-GAG) content of the extract is determined using the 1,9-dimethylmethylene blue dye calorimetric assay with chondroitin-6-sulfate as a standard. Acid hydrolysis is used to evaluate the amount of collagen, based on the content of hydroxyproline, using a 1:7.64 hydroxyproline-to-collagen mass ratio or approximately 13.5% of the total collagen content.

The compressive Young's modulus of cartilage is then measured by unconfined compression. Stress-strain curves are generated by compressing the constructs (i.e. at 0.01% strain per second, up to 150 μm deformation, for up to 3,000 seconds) and the compression load is measured. Young's modulus is calculated from the linear slope of the stress-strain curves. Also, the normal force, frictional force, axial deformation, and friction coefficient between cartilage and glass are measured in an unconfined compression configuration. A push-out is then used to test the integration strength between the fused CMBs and the native cartilage matrix.

The load bearing capabilities of the implant are quantified to determine the effects of loading on integration with the surrounding cartilage and the underlying bone and to examine "failure" parameters over time. Dynamic loading is performed using 10-15% surface-to-surface deformation at 1 Hz for up to 4 hours/day, 5-7 days/week. The effects of dynamic loading on extracellular matrix composition and distribution (via biochemistry and histology) and the functional properties (via unconfined compression testing) of the resultant tissue are assessed, as outlined above.

Methods of preparing and administering CMBs in hydrogel are optimized as needed to achieve significant improvements in mechanical and biochemical properties of the resultant tissues with mechanical stimulation, particularly (i) formation of a dense cartilage tissue (containing 3-6% w/w GAG and >5% w/w collagen) to fill the defect, (ii) physiologic mechanical properties (Young's moduli >800 kPa, friction coefficient <0.3), and (iii) integration of the developed product with adjacent cartilage and subchondral bone tissue.

Example 3: Long-Term Release of Growth Factor (TGF β3 and BMP6) and CMB Chondrogenesis Using PLGA Microspheres as a Delivery Platform To sustain long-term release of growth factors from the osteochondral grafts, control-release technology is incorporated and tested. In the test samples, microspheres are used to deliver growth factors to induce and enhance chondrogenesis. In the control samples, no microspheres are used.

The microspheres are made with PLGA-based polymers, which have been used as a viable protein delivery vehicle for their biocompatibility, injectability, and customizable release profiles. The controlled release profiles of the growth factor (GF) are optimized, with such profiles depending on many factors including biochemical properties of the selected GF.

PLGA microspheres are created using water-in-oil (w/o/w) emulsion method based on published protocols. Briefly, PLGA (50:50 lactic to glycolic acid ratio) and aqueous solution of GF are mixed in dichloromethane. The mixtures are homogenized to form a water-in-oil emulsion, which is added to polyvinyl alcohol (PVA) to form double emulsions. After prolonged stirring, the content is centrifuged to remove the supernatant. The microsphere pellet is then washed and lyophilized.

Scanning electron microscopy is used to assess the quality of the produced microspheres by characterizing them based on size distribution and morphologic properties of different microsphere groups. To optimize for uniform GF release, microspheres are selected that demonstrate the most uniform particle size and distinct individual spherical morphology. The GF release of different microspheres is analyzed by following published protocols. Briefly, 10 mg of microspheres are suspended in PBS in microcentrifuge tubes. To optimize the GF cargo, prepared microspheres are loaded with different combinations of BMP6 and TGFβ3 (5 mg:5 mg, 3 mg:7 mg, and 7 mg:3 mg). GF release is examined at 30 minutes, 1 hour, 5 hours, 1 day, 3 days, 7 days, and every 7 days thereafter. For every time point, supernatant is collected and equal volume of fresh PBS are added to the microspheres. This procedure is repeated until no pellet is present in the samples, indicating complete degradation of the microspheres and growth factor release. ELISA is performed on the collected supernatant to determine the concentration of growth factor release over time. Microspheres are selected for that can sustain long-term GF release at optimal concentration (10 ng/ml) for CMB chondrogenesis.

Conditions are optimized to prepare polymer microspheres having a long storage life. The shelf life of produced microspheres is tested at both 4° C. and 25° C. (room temperature) and the GF release profiles are assessed at different storage times. The GF microspheres are stored at 4° C. and 25° C. for 1 day, 7 days, 14 days, and 21 days and the GF release profiles evaluated to determine an acceptable range for storage at 4° C. and 25° C.

The growth factor (GF)-infused microspheres are analyzed in vitro to determine if they could sustain long-term GF release and therefore enhance CMB maturation and chondrogenesis. In this experiment, a hydrogel+CMBs±GF microsphere composite is made by mixing the components and injecting the composite into a custom mold. The composite constructs are cultured in an optimized medium (according to Examples 1 and 2) without supplementing with GF. Histology and biochemical assays are performed to confirm the role of GF release in CMB maturation, chondrogenesis, and osteochondral ECM deposition in the composite constructs. Conditioned medium of these constructs is collected at 30 minutes, 1 hour, 5 hours, 1 day, 3 days, 5 days, 7 days, and every 7 days to examine GF release over 5 weeks via ELISA. The composite constructs (hydrogel+CMBs+GF microspheres) may exhibit a degree of CMB maturation and chondrogenesis comparable to that of hydrogel+CMBs constructs, which are cultured in medium supplemented with BMP6 and TGF-β3.

Example 4: Model of Product Administration and Efficacy in an In Vitro Cartilage Defect Model Once protocols from Examples 1-3 have been optimized and suitable conditions and components selected for, the selected materials made from CMBs, hydrogel and GF-infused microparticles are tested in an in vitro cartilage defect model. The selected materials are injected into an explant cartilage defect model and cultured under mechanical loading as described in Examples 1 and 2. The explants are grown in chondrogenic medium without exogenous GF supplementation for up to five weeks. The resultant tissues are assessed for functionality as outlined in Examples 1 and 2. Additionally, GF-release into the media is assessed at each media change to further determine the efficacy of these platform for long-term treatment of PTOA. Histological, biochemical, and mechanical analyses are also performed to assess biologic and mechanical properties of the composite constructs. The success criteria are determined by formation of cartilage tissue in the defect and integration of the tissue to adjacent cartilage and subchondral bone.

Example 5: Testing Cryopreservation Effects on Chondrogenesis

The effects of cryopreservation on ADSC-mediated chondrogenesis was tested as outlined in FIG. 1. In FIG. 1, cells were cryopreserved during the two-dimensional (2-D) or three-dimensional (3-D) stages of CMB cultivation. For 2-D conditions, cells were either (i) passaged to P4 without cryopreservation (Fresh), (ii) cryopreserved immediately after harvesting the stromal vascular fraction (SVF), thawed, and passaged to P4 (SVF Cryo), or (iii) passaged to P1, cryopreserved, thawed, and passaged to P4 (P1 Cryo). As for 3-D conditions, CMBs were either maintained and not cryopreserved after formation (control), or cryopreserved after three days of cultivation and thawed one to five weeks after cryopreservation.

Frozen and control "Fresh" samples were prepared by centrifuging a sample of adipose tissue to isolate the stromal vascular fraction (SVF). The SVF was transferred to a flask and passaged four times with TrypLE-Select. Then the sample was separated into (i) a control sample that does not undergo cryopreservation and (ii) a frozen sample, with the frozen sample cryopreserved as described in Example 1 and stored in liquid nitrogen for one to five weeks. The cryopreserved sample was then thawed to yield the frozen sample. Both the control and test samples were then subject to further assays.

Test and control "SVF Cryo" samples were prepared by centrifuging a sample of adipose tissue to isolate the stromal vascular fraction (SVF). The SVF was cryopreserved as described in Example 1 and stored in liquid nitrogen for at least one month. The SVF is then thawed, transferred to a flask and passaged four times. Then, the sample was separated into a control and a frozen sample, with the frozen sample cryopreserved as described in Example 1. Then the sample was separated into (i) a control sample that does not undergo cryopreservation and (ii) a frozen sample, with the frozen sample cryopreserved as described in Example 1 and stored in liquid nitrogen for one to five weeks. The cryopreserved sample was then thawed to yield the test sample. Both the control and test samples were then subject to further assays.

Test and control "p1 Cryo" samples were prepared by centrifuging a sample of adipose tissue to isolate the stromal vascular fraction (SVF). The SVF was transferred to a flask and passaged once. The passaged SVF was cryopreserved as described in Example 1 and stored in liquid nitrogen for at least one month. The SVF was then thawed, transferred to a flask and passaged four times. Then the sample was separated into a control and a frozen sample, with the frozen sample cryopreserved as described in Example 1. Then the sample was separated into (i) a control sample that does not undergo cryopreservation and (ii) a frozen sample, with the frozen sample cryopreserved as described in Example 1 and stored in liquid nitrogen for one to five weeks. The cryopreserved sample was then thawed to yield the test sample. Both the control and test samples were then subject to further assays.

Figure 2:
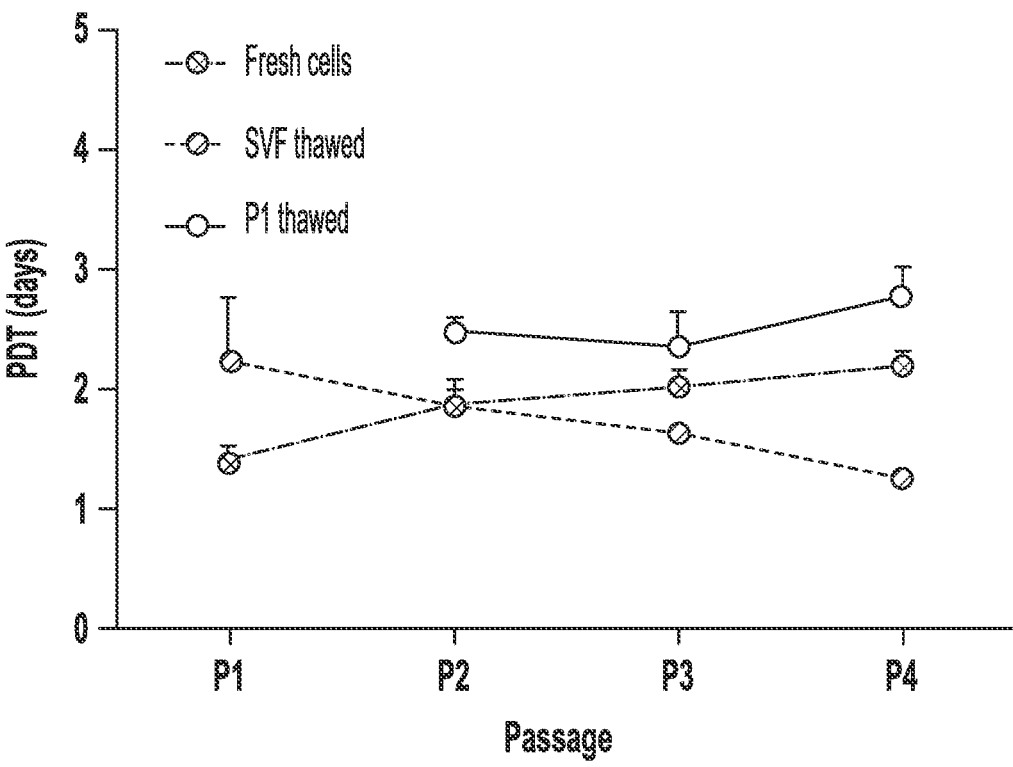
FIG. 2 shows a graph of population doubling time versus number of passages of adipocyte-derived stem cells (AD-SCs) in samples that were not cryopreserved (Fresh), that were cryopreserved immediately after harvesting, then thawed and passaged one to four times (SVF Cryo), and ADSCs that were passaged once, cryopreserved, thawed and passaged one to four times (P1 Cryo).

Then, the effects of ADSC cryopreservation on population doubling time were assayed for. A comparison was made among ADSCs that are (i) passaged to P4 without cryopreservation (Fresh), (ii) ADSCs that are cryopreserved immediately after harvesting stromal vascular fraction (SVF), thawed, and passaged to P4 (SVF Cryo), and (iii) ADSCs that are passaged to P1, cryopreserved, thawed, and passaged to P4 (P1 Cryo). Samples were taken at each of the four passages made after the last cryopreservation steps and were then assayed for population doubling time. The results are shown in FIG. 2, with the population doubling time on the Y-axis and the number of passages undertaken on the X-axis.

Analysis of the population doubling time (PDT) revealed that Fresh and P1 Cryo ADSCs exhibited similar trends where the PDT increased with passaging. Alternately, for SVF Cryo ADSCs, the PDT decreased with passage. For "Fresh" samples, the population doubling time increased from about 1.5 days (passaged once) to about 2 days when passaged four times. In contrast, for "SVF Cryo" samples in which SVF was cryopreserved and thawed, the population doubling time decreased from about 2 days (passaged once) to about 1.5 days when passaged four times. For "p1 Cryo" samples in which SVF was passaged once before being cryopreserved and thawed, the population doubling time was about 2.5 days and increased slightly with more passaging.

Example 6: Testing ADSC Cryopreservation Effects on Chondrogenesis

Figure 3:
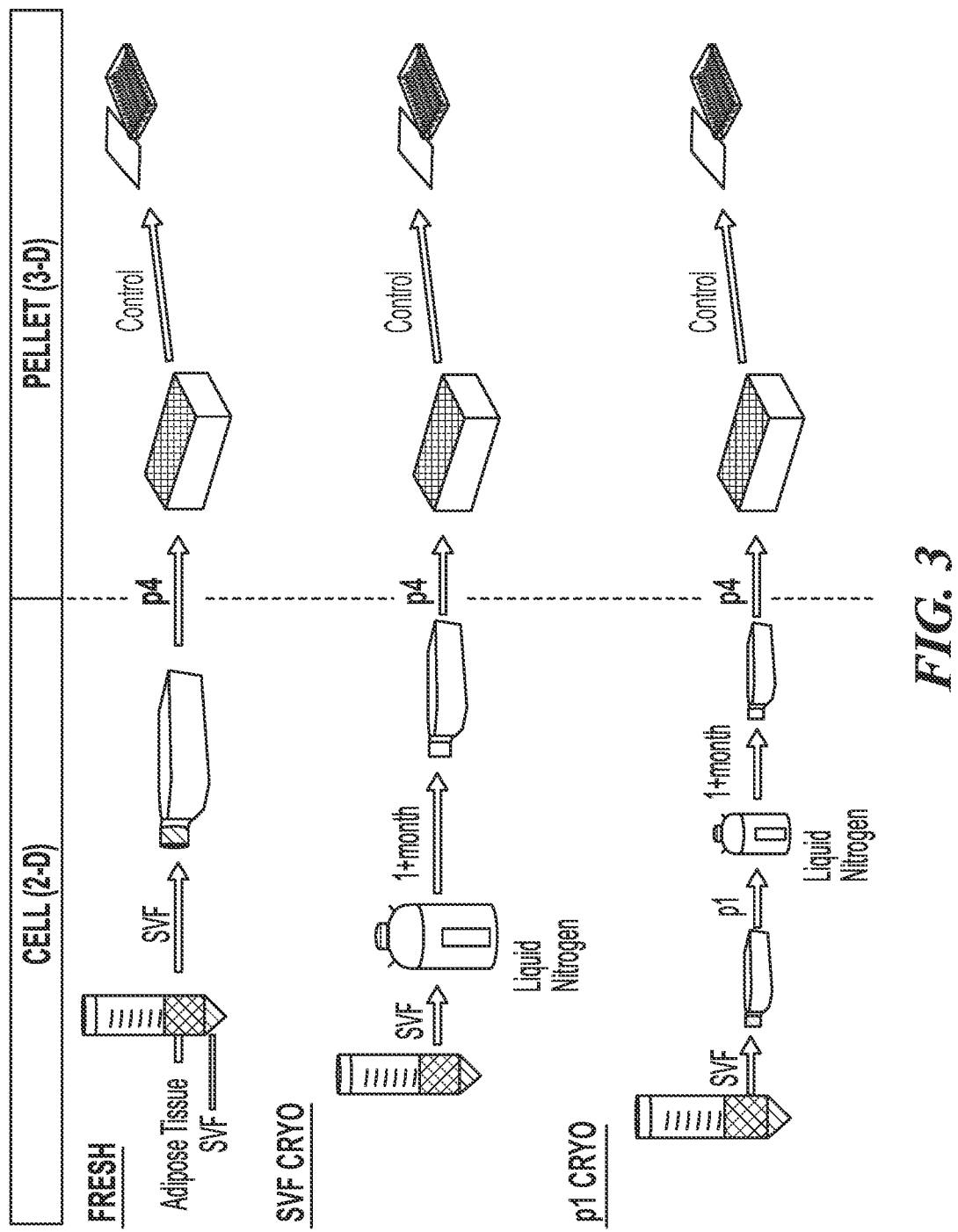
FIG. 3 shows a protocol for testing the effects of cryopreservation on ADSCs. The protocol is similar to that of FIG. 1, except that the CMBs are not cryopreserved.

Further assays of the effect of cryopreservation on cells (2D in flasks) were undertaken. Control "Fresh", "SVF Cryo", and "p1 Cryo" CMBs were prepared in the manner described above and as shown in FIG. 3. After 28 days in culture, the diameter of the CMBs in each of the "Fresh", "SVF Cryo", and "p1 Cryo" samples was measured and shown in FIG. 4A. Fresh CMBs have a diameter of approximately 1.9 mm, SVF Cryo CMBs have a diameter of approximately 1.7 mm, and P1 Cryo CMBs have a diameter of approximately 1.6 mm.

Figure 4A:
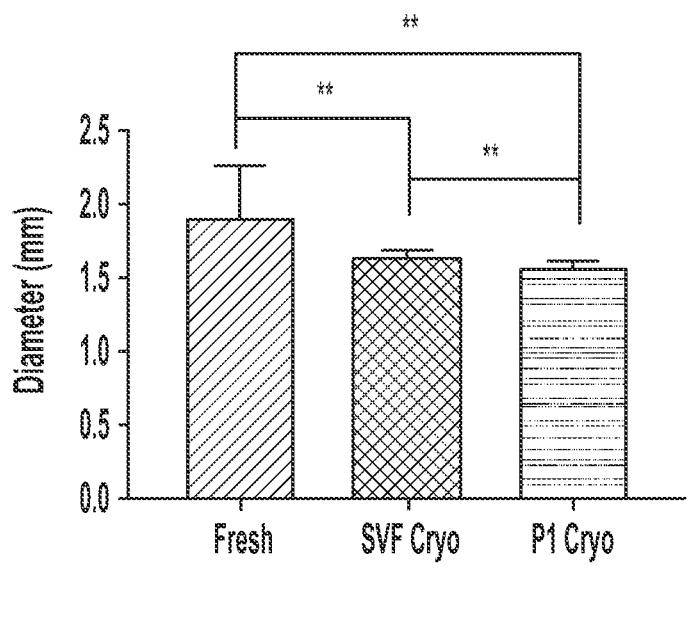
FIGS. 4A-4F show the results of testing for various parameters on Fresh, SVF Cryo and P1 Cryo ADSC populations. Test results are shown for diameter (FIG. 4A), wet weight (FIG. 4B), mass ratio of DNA to wet weight (FIG. 4C), mass ratio of GAG to wet weight (FIG. 4D), mass ratio of collagen to wet weight (FIG. 4E), and the appearance of each of Fresh, SVF Cryo, and P1 Cryo populations in culture (FIG. 4F). The scale bar in FIG. 4F is 0.5 mm.
Figure 4B:
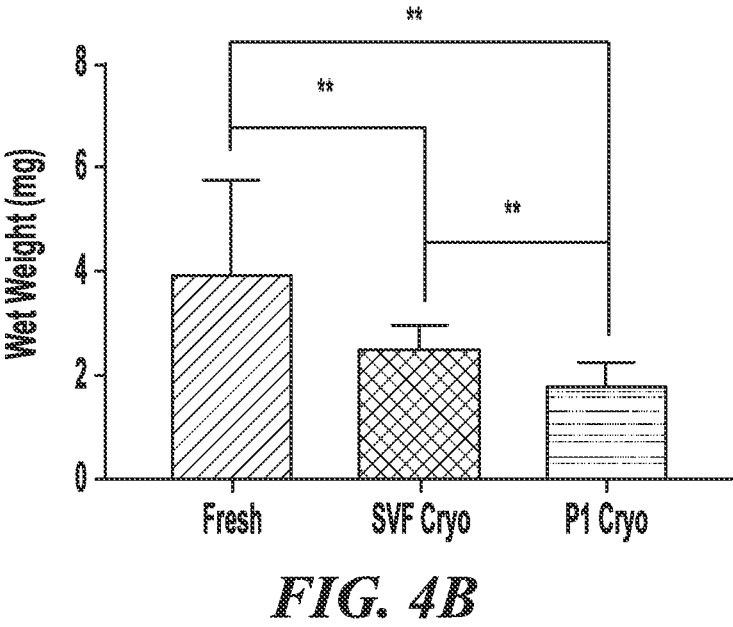

The wet weight of CMBs in each of the "Fresh", "SVF Cryo", and "p1 Cryo" samples was measured and shown in FIG. 4B after 28 days in culture. Fresh CMBs have a wet weight of approximately 4.0 mg. SVF Cryo CMBs have a wet weight of approximately 2.5 mg, and P1 Cryo CMBs have a wet weight of approximately 1.7 mg. (* $p<0.05$, ** $p<0.005$.)

Figure 4C:
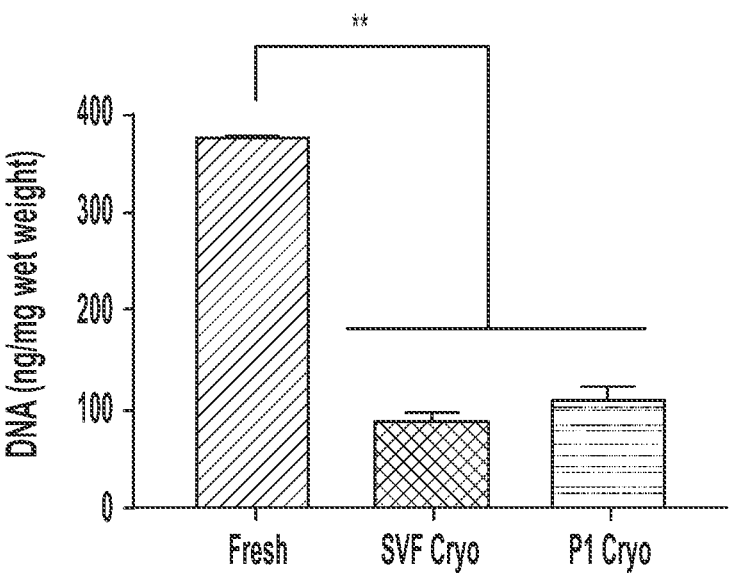

The mass ratio of DNA to wet weight (ng DNA/mg wet weight) in each of the "Fresh", "SVF Cryo", and "p1 Cryo" samples was measured and shown in FIG. 4C after 28 days in culture. Fresh CMBs have a mass ratio of approximately 375 ng DNA/mg wet weight. SVF Cryo CMBs have a mass ratio of approximately 85 ng DNA/mg wet weight. P1 Cryo CMBs have a mass ratio of approximately 105 ng DNA/mg wet weight. (* $p<0.05$, ** $p<0.005$.)

Figure 4D:
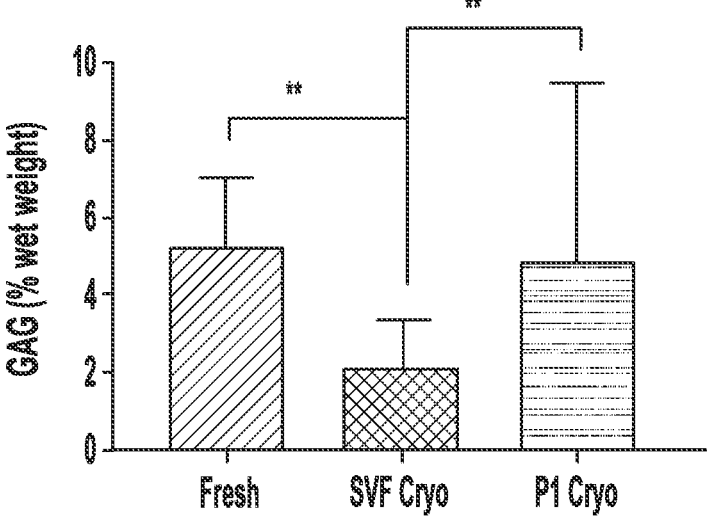

The mass ratio of GAG to wet weight (w/w %) in each of the "Fresh", "SVF Cryo", and "p1 Cryo" samples was measured and shown in FIG. 4D after 28 days in culture. Fresh CMBs have a ratio of approximately 5.5 w/w %. SVF Cryo CMBs have a ratio of approximately 2.0 w/w %. P1 Cryo CMBs have a ratio of approximately 4.8 w/w %. (* $p<0.05$, ** $p<0.005$.)

Figure 4E:
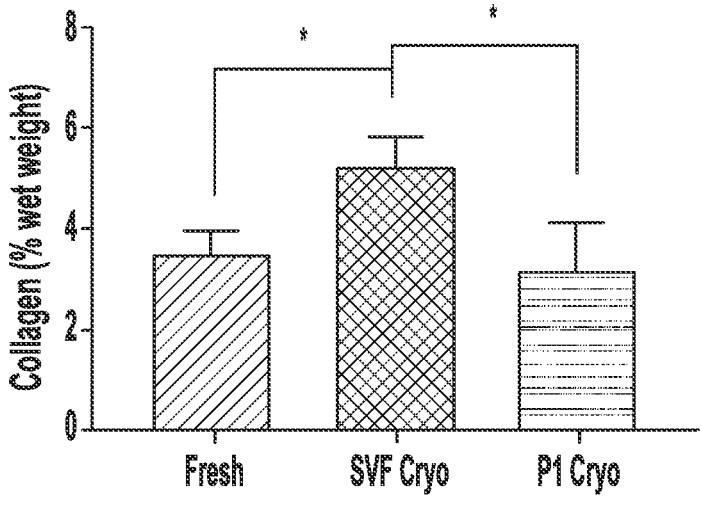

The mass ratio of collagen to wet weight (w/w %) in each of the "Fresh", "SVF Cryo", and "p1 Cryo" samples was measured and shown in FIG. 4E after 28 days in culture. Fresh CMBs have a ratio of approximately 3.5 w/w %. SVF Cryo CMBs have a ratio of approximately 5.2 w/w %. P1 Cryo CMBs have a ratio of approximately 3.1 w/w %. (* $p<0.05$, ** $p<0.005$.)

Figure 4F:
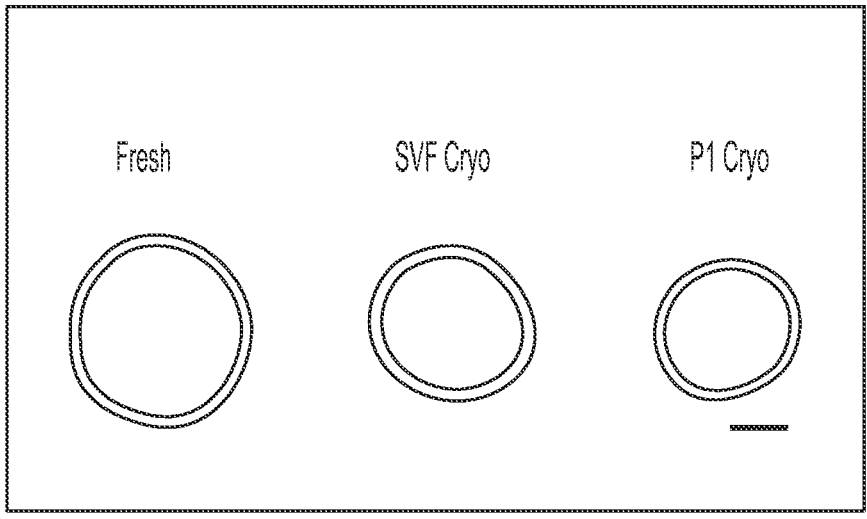

The appearance of each of the "Fresh", "SVF Cryo", and "p1 Cryo" CMBs is shown in FIG. 4F after 28 days in culture. The scale bar is 0.5 mm.

When the 3 groups of ADSCs were used to generate CMBs and grown in chondrogenic differentiation media (CDM) for 4 weeks, cryopreservation significantly decreased the diameter, wet weight and DNA of the resultant samples ($p<0.01$). While cryopreservation also significantly decreases GAG [($p<0.01$) marker for chondrogenesis] and significantly increases collagen content ($p<0.05$) in SVF Cryo CMBs, P1 Cryo CMBs had properties similar to those of Fresh CMBs. FIG. 4F shows images of typical CMBs after 28 days in culture.

The above results suggest that ADSCs that are cryopreserved after one passage ("p1 Cryo") are suitable for an off-the-shelf injectable product.

Example 7: Testing CMB Cryopreservation Effects on Chondrogenesis

Further assays of the effect of cryopreservation on CMB pellets (3-D in wells) were undertaken.

Figure 5:
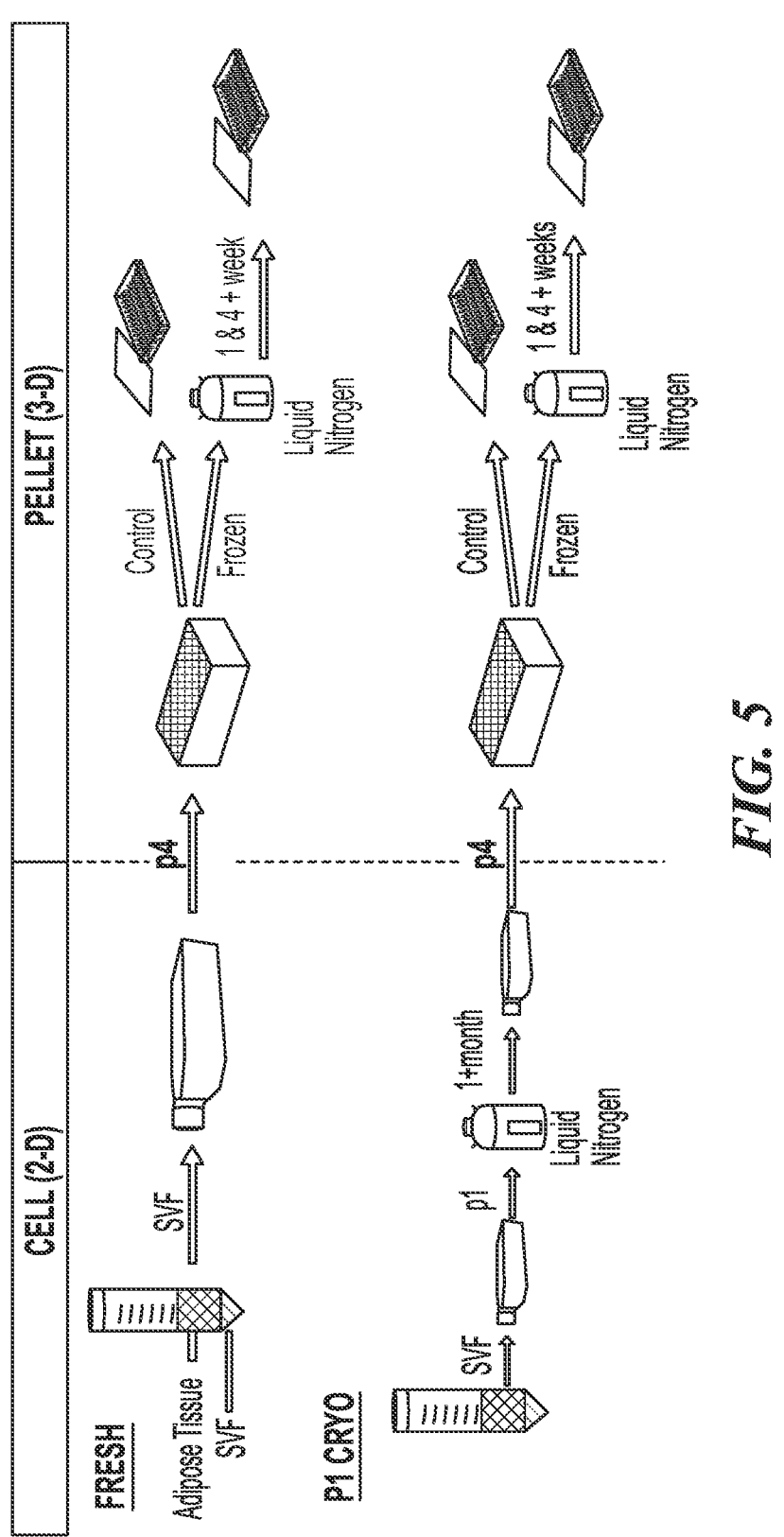
FIG. 5 shows a protocol for testing the effects of cryopreservation on pellets of condensed mesenchymal cell bodies (CMB) prepared from the ADSCs.

Control "Fresh" and "p1 Cryo" samples were prepared as shown in FIG. 5. A sample of adipose tissue was centrifuged to isolate the stromal vascular fraction (SVF). In the "p1 Cryo" sample, the SVF was placed in a flask, passaged once, then cryopreserved as described in Example 1, and stored in liquid nitrogen for one to five weeks. The cryopreserved sample was then thawed and passaged four times. In the "Fresh" sample, the SVF was placed in a flask and passaged four times.

Each of the "Fresh" and "p1 Cryo" samples were then split into control and frozen samples. The frozen sample was cryopreserved as described in Example 1 and stored in liquid nitrogen for at least one week. The frozen samples were then thawed, transferred to multi-well plates. Both the control and frozen samples are then subject to further assays.

Figure 6A:
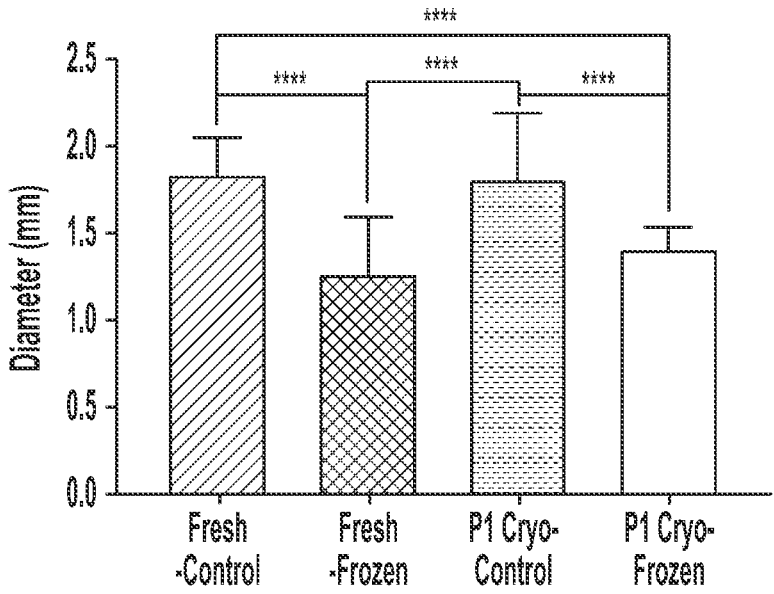
FIGS. 6A-6F show the results of testing for various parameters on Fresh, SVF Cryo and P1 Cryo ADSC populations. Test results are shown for diameter (FIG. 6A), wet weight (FIG. 6B), mass ratio of DNA to wet weight (FIG. 6C), mass ratio of GAG to wet weight (FIG. 6D), mass ratio of collagen to wet weight (FIG. 6E), and the appearance of each of Fresh, SVF Cryo, and P1 Cryo populations in culture (FIG. 6F).

After three days in culture in multi-well plates (3-D culture) and after 28 days of chondrogenic differentiation, the diameter of CMBs in each of the "fresh-control", "p1 Cryo-control", "fresh-frozen" and "p1 Cryo-frozen" samples was measured, with results shown in FIG. 6A. Fresh-control CMBs have a diameter of approximately 1.87 mm, fresh-frozen CMBs have a diameter of approximately 1.20 mm, p1 Cryo-control CMBs have a diameter of approximately 1.82 mm, and p1 Cryo-frozen CMBs have a diameter of approximately 1.43 mm.

Figure 6B:
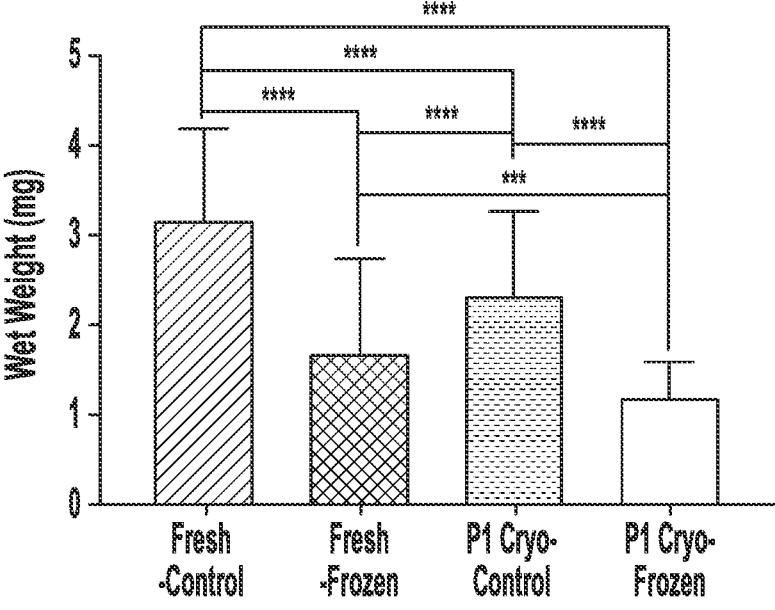

The wet weight of cells in each of the "fresh-control", "p1 Cryo-control", "fresh-frozen" and "p1 Cryo-frozen" samples was also measured, with results shown in FIG. 6B. Fresh-control CMBs have a wet weight of approximately 3.15 mg, fresh-frozen CMBs have a wet weight of approximately 1.70 mg, p1 Cryo-control CMBs have a wet weight of approximately 2.30 mg, and p1 Cryo-frozen CMBs have a wet weight of approximately 1.20 mg.

Figure 6C:
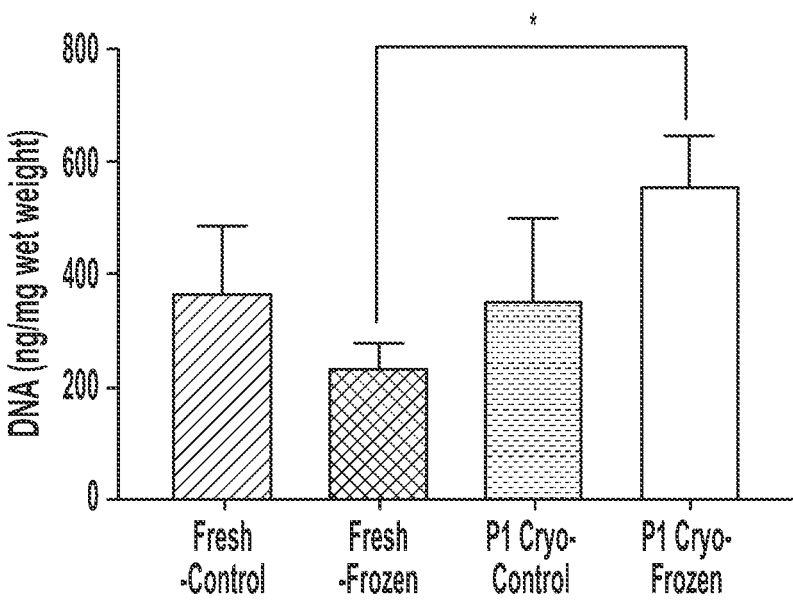

The mass ratio of DNA to wet weight (ng DNA/mg wet weight) in each of the "fresh-control", "p1 Cryo-control", "fresh-frozen" and "p1 Cryo-frozen" samples was measured and shown in FIG. 6C. Prior to long-term chondrogenic induction, CMB has a DNA to wet weight mass ratio of approximately between 200 to 5000 ng DNA/mg CMB. After chondrogenic induction for 5 weeks, fresh-control CMBs have a DNA to wet weight mass ratio of approximately 360 ng DNA/mg wet weight, fresh-frozen CMBs have a mass ratio of approximately 230 ng DNA/mg wet weight, p1 Cryo-control CMBs have a mass ratio of approximately 345 ng DNA/mg wet weight, and p1 Cryo-frozen CMBs have a mass ratio of approximately 550 ng DNA/mg wet weight.

Figure 6D:
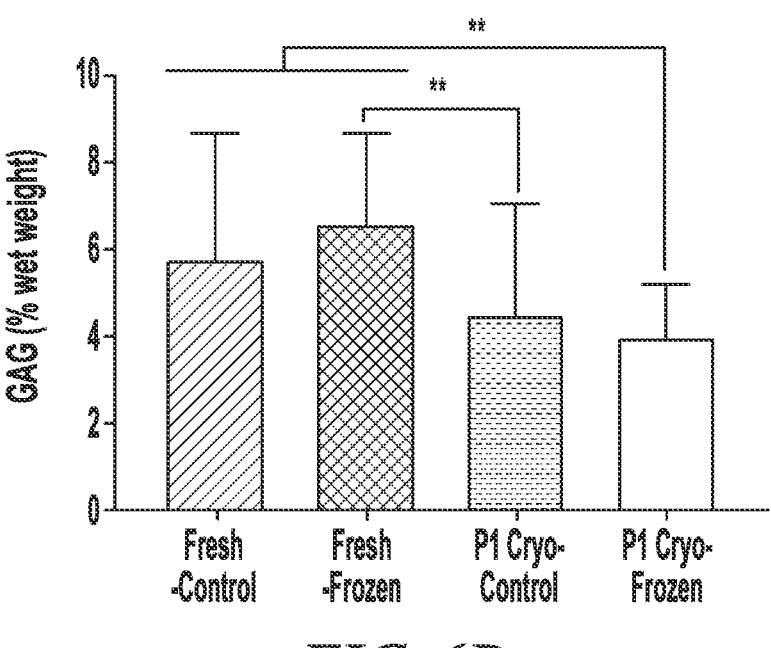

The mass ratio of GAG to wet weight (w/w %) in each of the "fresh-control", "p1 Cryo-control", "fresh-frozen" and "p1 Cryo-frozen" samples was measured and shown in FIG. 6D. Fresh-control CMBs have a mass ratio of approximately 5.70 (w/w %), fresh-frozen CMBs have a mass ratio of approximately 6.55 (w/w %), p1 Cryo-control CMBs have a mass ratio of approximately 4.45 (w/w %), and p1 Cryo-frozen CMBs have a mass ratio of approximately 3.90 (w/w %).

Figure 6E:
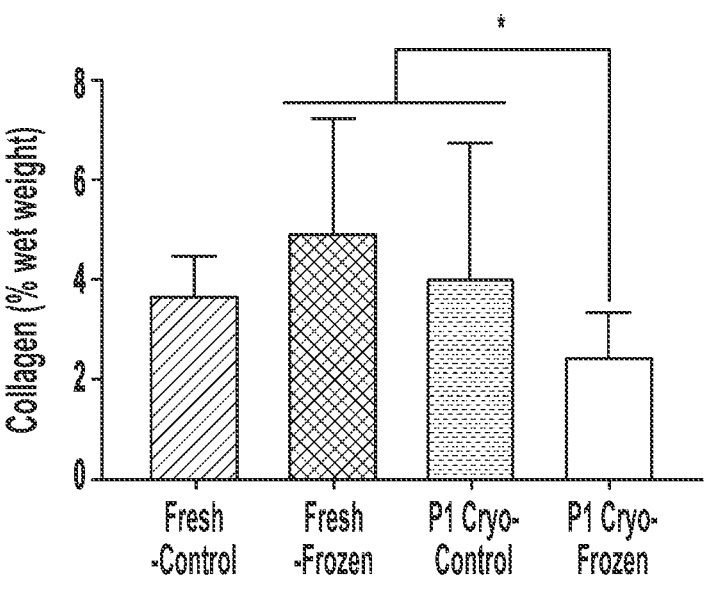

The mass ratio of collagen to wet weight (w/w %) in each of the "fresh-control", "p1 Cryo-control", "fresh-frozen" and "p1 Cryo-frozen" samples was measured and shown in FIG. 6E. Fresh-control CMBs have a mass ratio of approximately 3.65 (w/w %), fresh-frozen CMBs have a mass ratio of approximately 4.95 (w/w %), p1 Cryo-control CMBs have a mass ratio of approximately 4.00 (w/w %), and p1 Cryo-frozen CMBs have a mass ratio of approximately 2.40 (w/w %).

Figure 6F:
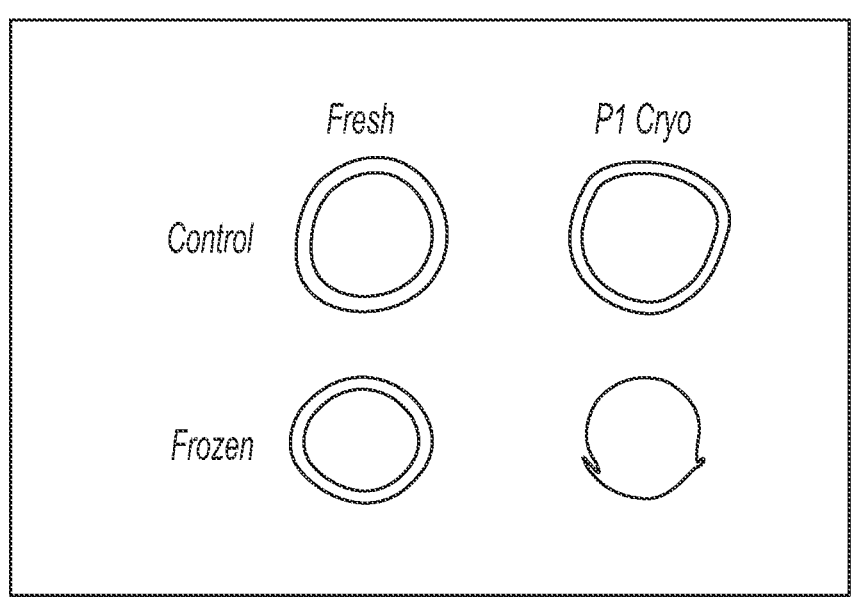

The appearance of each of the "fresh-control", "p1 Cryo-control", "fresh-frozen" and "p1 Cryo-frozen" CMBs is shown in FIG. 6F after three days in culture in multi-well plates (3-D culture) and after 28 days of chondrogenic differentiation.

The diameters (FIG. 6A) are similar for the control CMB with a 25-30% reduction in diameter with CMB cryopreservation. These differences are seen by the visual inspection data in FIG. 6F. The wet weight data in FIG. 6B shows a significant difference among all groups, with significant reductions seen with both ADSC and CMB cryopreservation.

Biochemical analysis of the DNA (FIG. 6C), GAG (FIG. 6D) and collagen (FIG. 6E) contents showed disparate responses depending on the perimeter in question. The DNA content of the CMBs was not significantly different between the Fresh-Control, Fresh-Frozen and P1 Cryo-Control groups. In the P1 Cryo-Frozen group, however, there was an increase in the DNA content compared to the other groups, particularly Fresh-Frozen. The GAG content was lower for the P1 Cryo CMBs compared to the Fresh CMBs. Some of these differences are significant, as outlined in FIG. 6D. The fibrillar collagen contents were similar between the control groups, however there was an increase in the collagen content of the Fresh-Frozen group with a concomitant decrease in collagen content in the P1 Cryo-Frozen group compared to their respective controls.

Example 8: Flow Cytometry Analysis of Chondrogenic CMBs

Figure 7A:
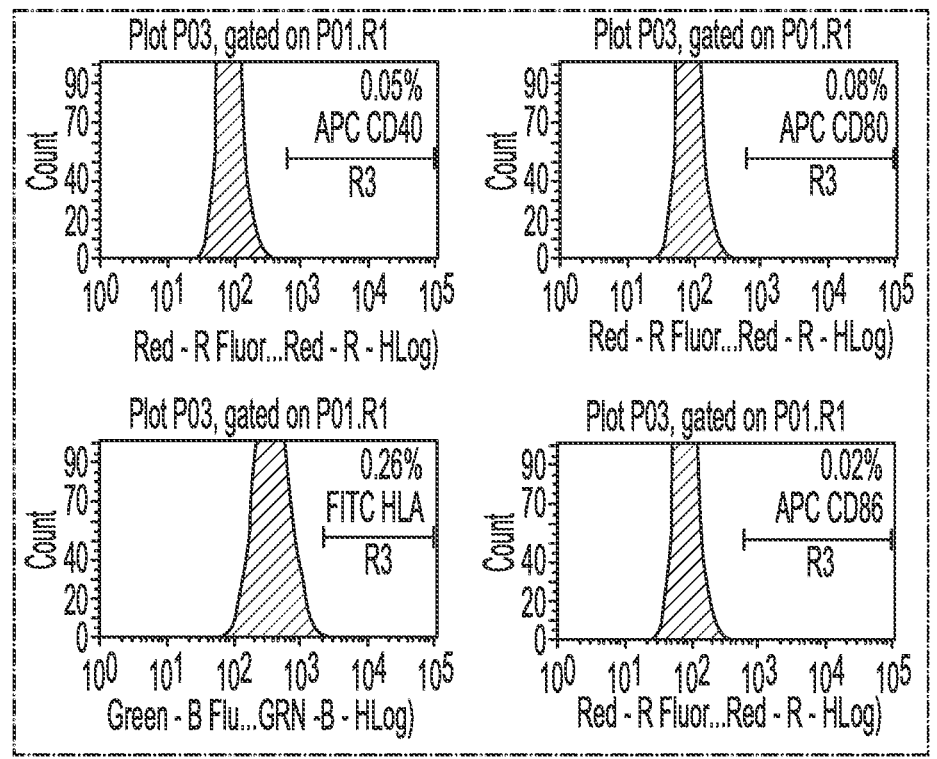
FIG. 7A shows results of assaying for various antigens on chondrogenic CMBs by flow cytometry. Negative expression was seen with the ISO antibodies used as negative controls, while positive expression was seen with CD59 and CD90 used as positive controls. The expression of tested immunogenicity markers HLA Class II, CD40, CD80 and CD86 was negative.
Figure 7A:
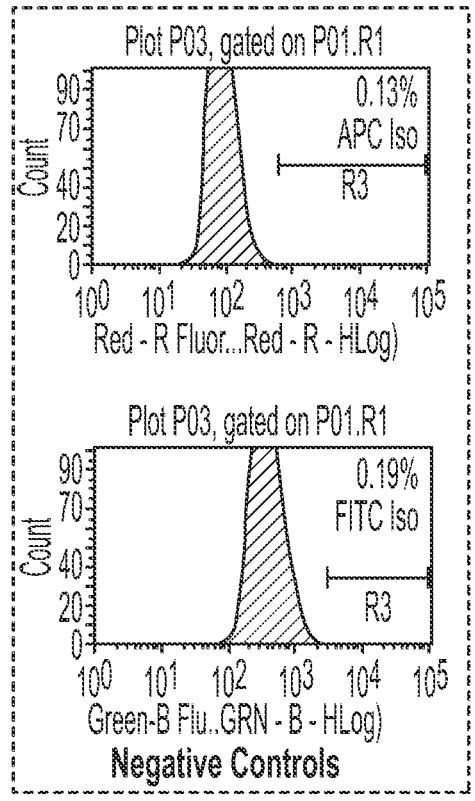
Figure 7A:
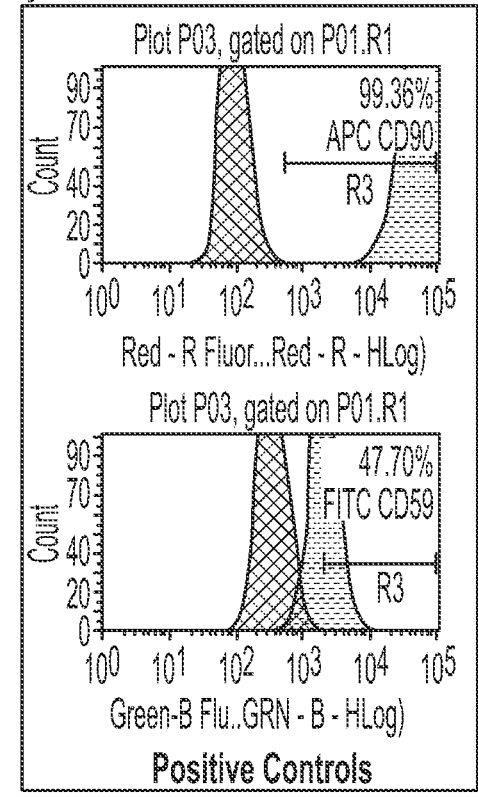

Analysis of cell surface markers of chondrogenic CMBs was undertaken by flow cytometry. Antibodies against ISO were used as negative controls, with antibodies against CD59 and CD90 used as positive controls. Expression of HLA class II, CD40, CD80 or CD86 was tested. Also, expression of CD34, CD45, CD73, CD90 and CD105 was tested. In FIG. 7A, the flow cytometry results show the antigenicity of chondrogenic CMBs via negative HLA Class II, CD40, CD80 and CD86 expression. Negative expression was also seen with the ISO antibodies used as negative controls, while positive expression was seen with CD59 and CD90 used as positive controls.

Figure 7B:
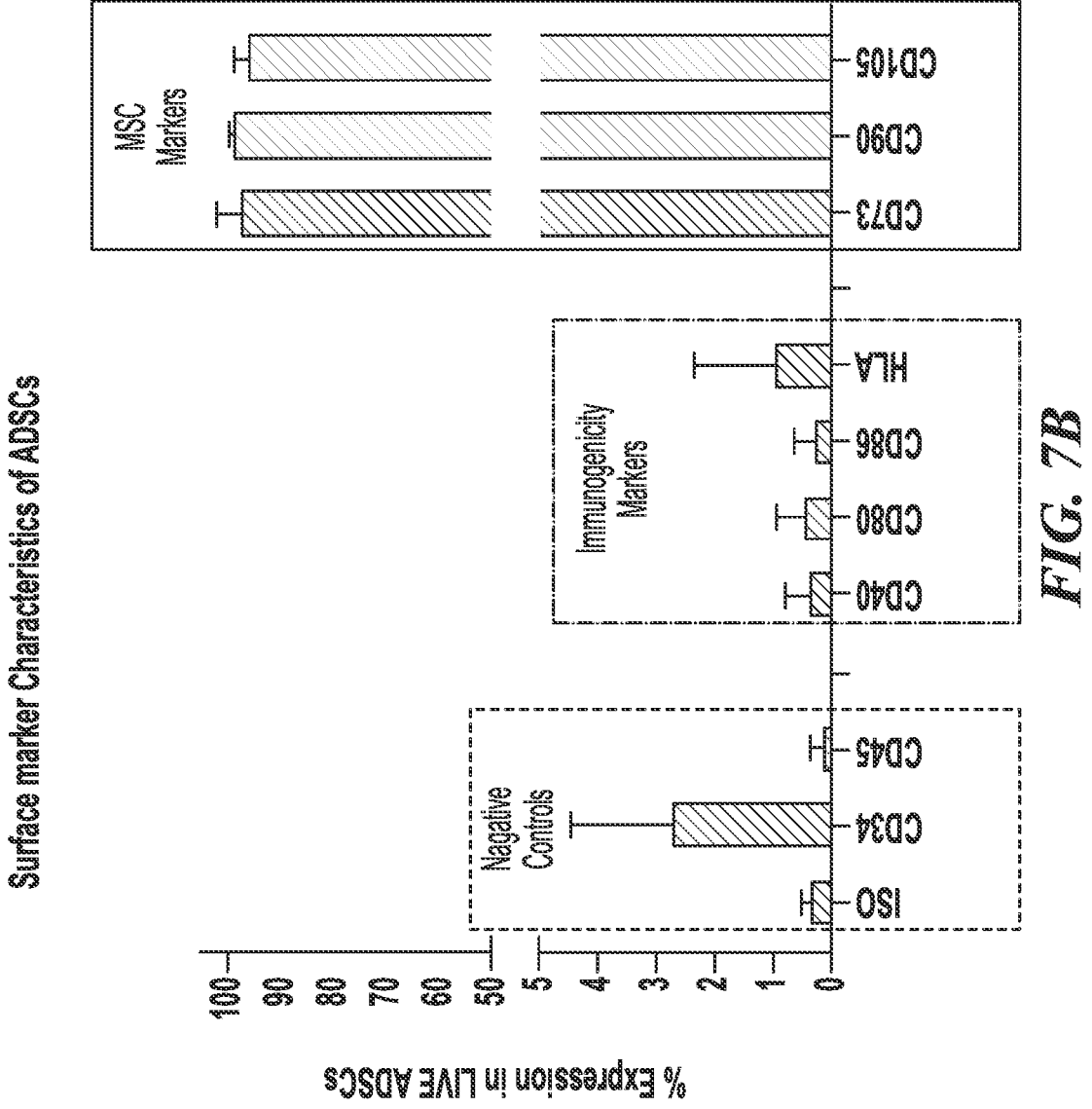
FIG. 7B shows the expression levels of various antigens on live ADSCs.

FIG. 7B shows the percent expression of various antigens on live ADSCs after analysis of surface markers characteristics was undertaken by flow cytometry. The ADSCs were taken from four human donors. The typical mesenchymal stem cell (MSC) profile was seen in which there was low expression of CD34 and CD45 with concomitant high expression of CD73, CD90 and CD105. Furthermore, examination of antigenic markers in cryopreserved CMBs showed a lack of HLA class II, CD40, CD80 or CD86 expression, indicating that such cells are not likely to elicit an immunogenic response.

Example 9: Silicone Defect Model to Test Combinations of Hydrogels and CMBs

Figure 8:
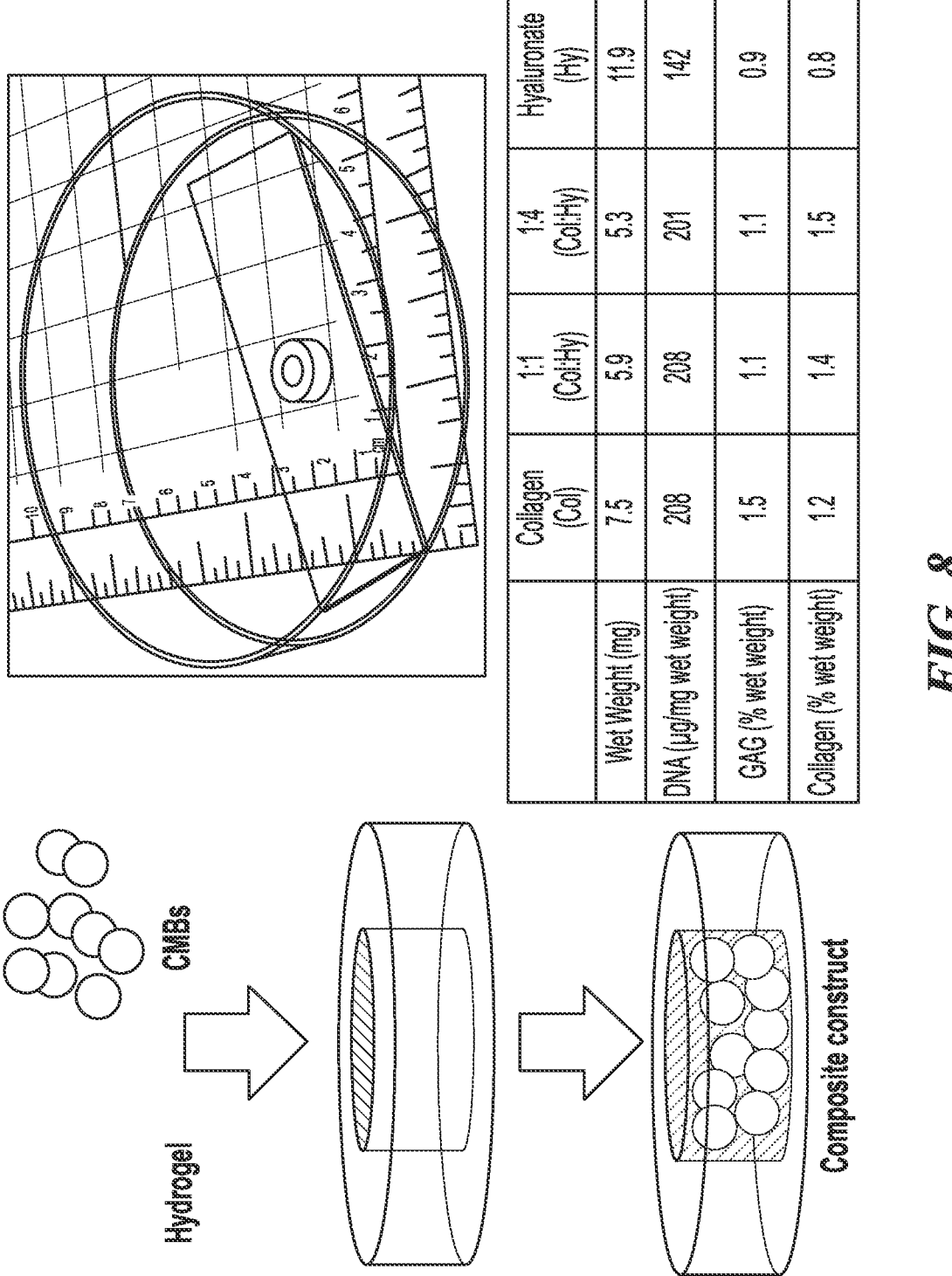
FIG. 8 shows the experimental protocol of testing combinations of hydrogels and CMBs in a silicone explant defect model.

Type I collagen, hyaluronic acid, and type I collagen: hyaluronate (in ratios of 4:1, 1:1, and 1:4) are examined as delivery vehicles for CMBs and growth factor-microparticles. For the optimization of our hydrogel delivery vehicle as well as CMB and microparticle parameters, a silicone rubber rings method (5-mm inner diameter, 2-mm thickness) that mimics an explant defect model is used, as shown in FIG. 8. A hydrogel and CMBs are added to the silicone defect. The wet weight, DNA mass ratio, GAG mass ratio and collagen mass ratio parameters are shown in the table in FIG. 8, all gels formulations are suitable options to deliver CMBs. Optimization of the concentrations and time for gelation for each hydrogel is undertaken in the silicone defect model. Additional optimization is conducted in both the silicone and cartilage defect models, filled with CMB delivered with (i) collagen and (ii) collagen:hyaluronate (1:1, 4:1, and 1:4), to determine which condition gives the best combination of cartilaginous phenotype and integration with the surrounding cartilage.

Figures 9A, 9B, 9C:
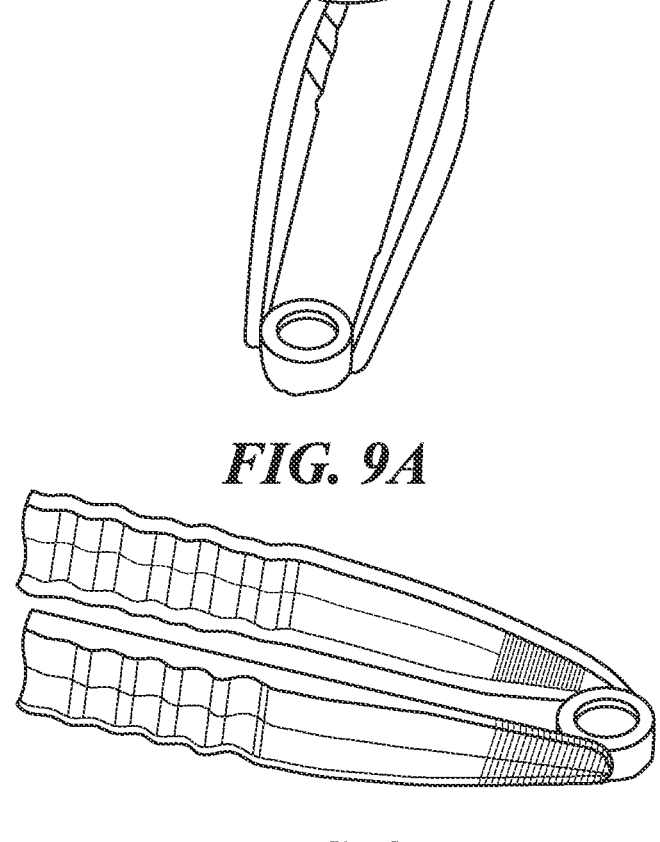
FIG. 9A is a photograph of an empty defect in an osteochondral defect model.
FIG. 9B is a photograph showing a collagen gel-CMB filled defect.
FIG. 9C is a photograph showing a hemisection of collagen gel-CMB filled defect, with retention of the fill component within the defect.

After optimization in the silicone defect model, testing is repeated using an osteochondral defect model. FIG. 9A is a photograph of an empty defect in an osteochondral defect model. FIG. 9B is a photograph showing a collagen gel-CMB filled defect. FIG. 9C is a photograph showing a hemi-section of collagen gel-CMB filled defect, with retention of the fill component within the defect. Additional optimization of the above-described parameters is performed in the osteochondral defect model.

Figure 10A:
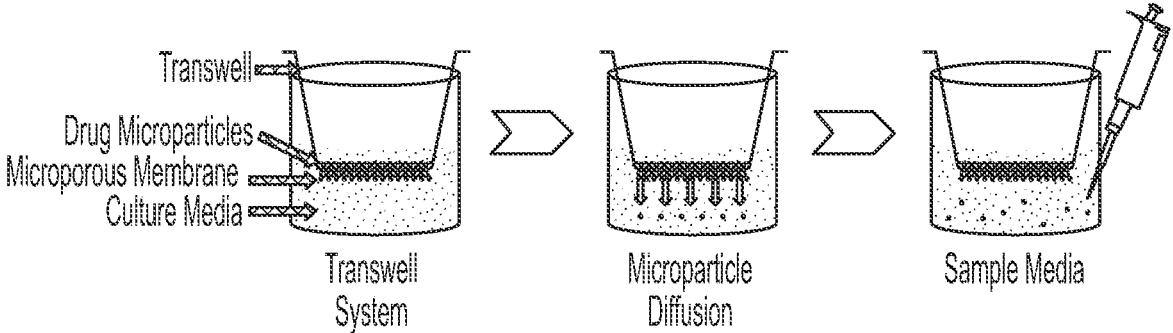
FIG. 10A shows an experimental protocol for examining drug release over time.

Example 10: Silicone Defect Model to Test Combinations of Hydrogels and CMBs A drug was incorporated into CMB-hydrogel combinations to test whether it can induce hADSC chondrogenesis. The drug release formulation is designed to be equivalent to the drug supplement method previously used for inducing hADSC chondrogenesis where the drugs were added directly to the chondrogenic differentiation medium. Particles having an average 1-10 μm size were loaded with 0.02% (w/w %) drug. 80 mg of drug-loaded microparticles were fabricated and tested for long-term drug release (up to 35 days) to determine the optimal microparticles concentration needed to successfully induce hADSC chondrogenesis. Drug release over time was assayed for using the experimental protocol described in FIG. 10A.

Figure 10B:
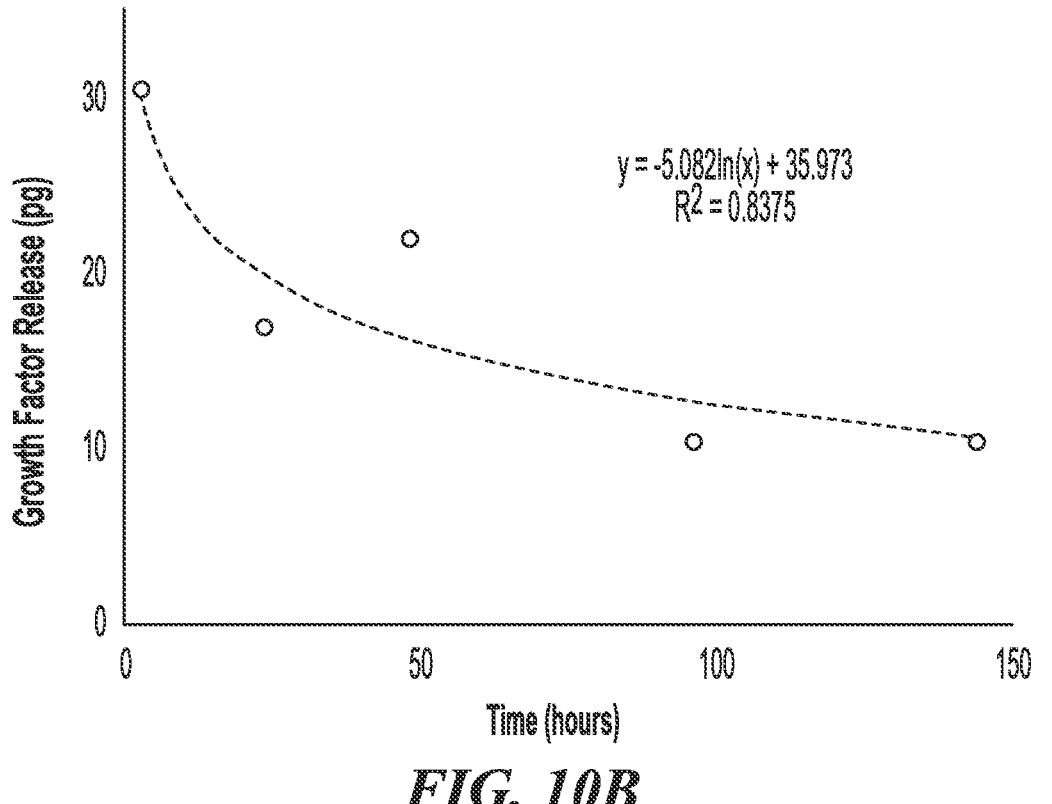
FIG. 10B shows the observed release of growth factor over time.

FIG. 10B shows the observed release of the drug over time. 10 mg of microparticles provide a release rate of about 10 pg/48 hours, or 5 pg/day, over six days.

To achieve a 20 pg/day release rate suitable for maintaining a 10 ng/ml growth factor concentration with a 5 mm diameter/1 mm thick graft (20 μl graft volume), 40 mg of microparticles may be loaded into each graft.

Example 11: Cartilage Explant Defect Model to Test Regeneration of Cartilage from a Composition Comprising Hydrogels, CMBs and Drugs Two drugs, TGF-β3 and BMP-6, were added to CMB-hydrogel combinations to test whether they fill a cartilage defect in an ex vivo model and whether dynamic deformational loading affects the content of GAGs and collagen. Dynamic deformational loading (1% tare load followed by 10% surface-to-surface displacement at 1 Hz for 3 hours per day, 5-7 days/week [Ng et al., Cell Mol. Bioeng., Sep. 1, 2009, 2(3):386-394]) was used to stimulate ADSC to differentiate into chondrocytes and to increase production of chondrogenic differentiation factors such as glycosaminoglycans, cartilage oligomeric protein (COMP), link protein, hyaluronic acid, and collagens especially type II collagen, type IX collagen, type XI collagen. The GAG content and collagen content of cartilage filler that underwent dynamic deformational loading and control cartilage filler were assayed. The results are shown in FIGS. 11A and 11B.

Figure 11A:
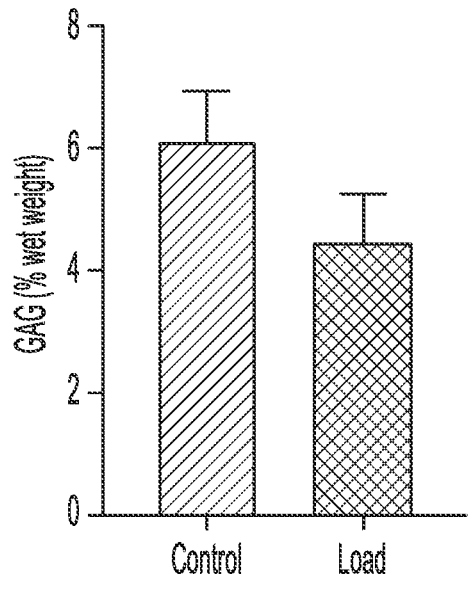
FIG. 11A shows that the GAG content was similar for both loaded and unloaded control cartilage filler.

FIG. 11A shows that the GAG content was similar for both loaded and unloaded control cartilage filler.

Figure 11B:
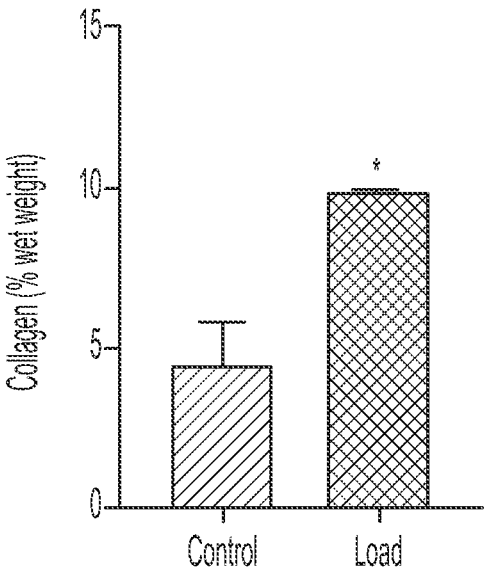
FIG. 11B shows loading improve collagen content to 10% of the wet weight compared to unloaded control which at about 5% collagen by wet weight.
Figure 12:
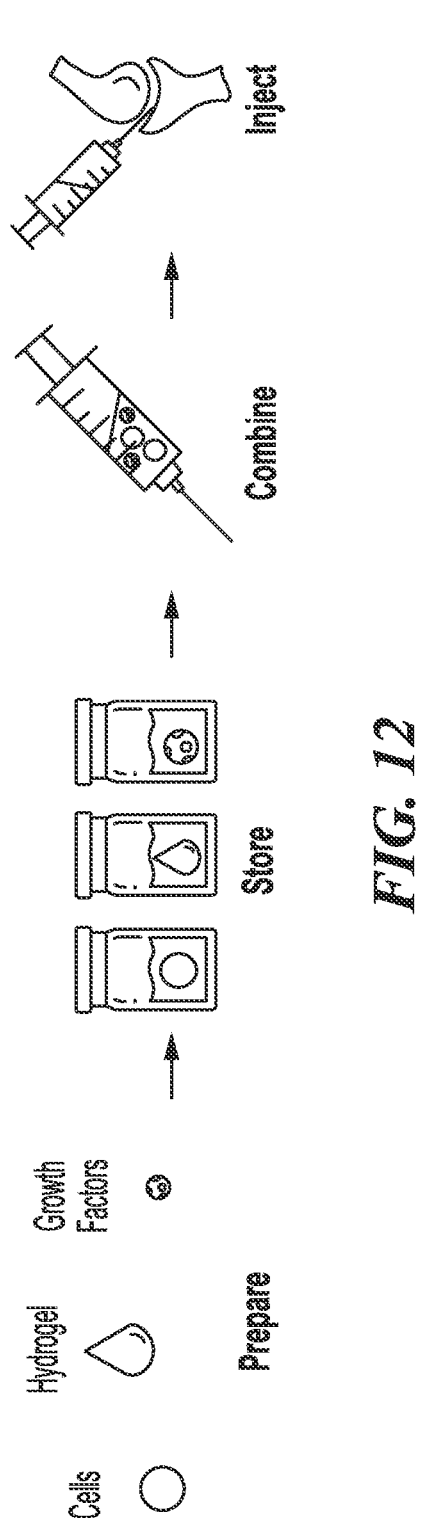
FIG. 12 shows a schematic manufacturing and delivery processes of a cartilage filler product. Individual cell, hydrogel, and growth factor components are prepared, stored until needed, and then combined in a syringe for injection into the defect site.

FIG. 11B shows loading improve collagen content to 10% of the wet weight compared to unloaded control which at about 5% collagen by wet weight.

Example 12: Cartilage Explant Defect Model to Test the Delivery of Various Hydrogel Compositions Different compositions and concentrations of hydrogel were tested for retention and gelation time in a full-thickness cartilage explant defect model. The gel components tested included fibrin only, and various combinations of collagen/hyaluronan. Gel retention capacity was tested by delivering various hydrogel compositions into explant defects, curing, and then agitating at 37° C. in PBS for up to 5 days.

Figure 13:
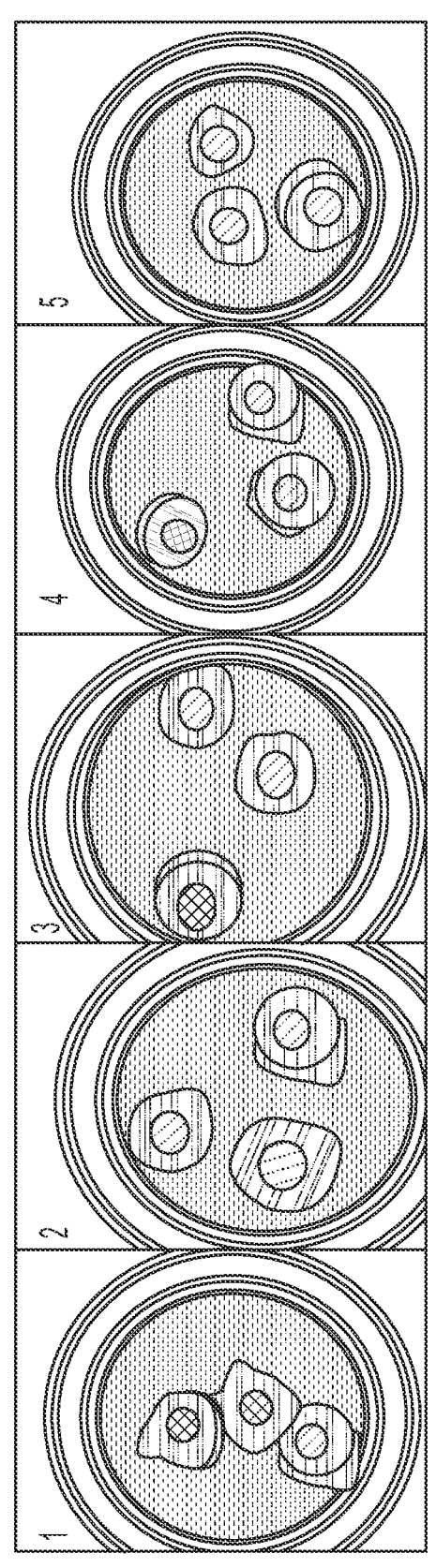
FIG. 13 shows the delivery of fibrin and various hyaluronan/collagen hydrogel formulations into bovine cartilage explant defects. Compositions differ in opacity and retention.

The results are shown in FIG. 13. The fibrin only and high hyaluronan hydrogel compositions exhibited superior retention, as compared to the high collagen composition samples.

Figures 14, 15A:
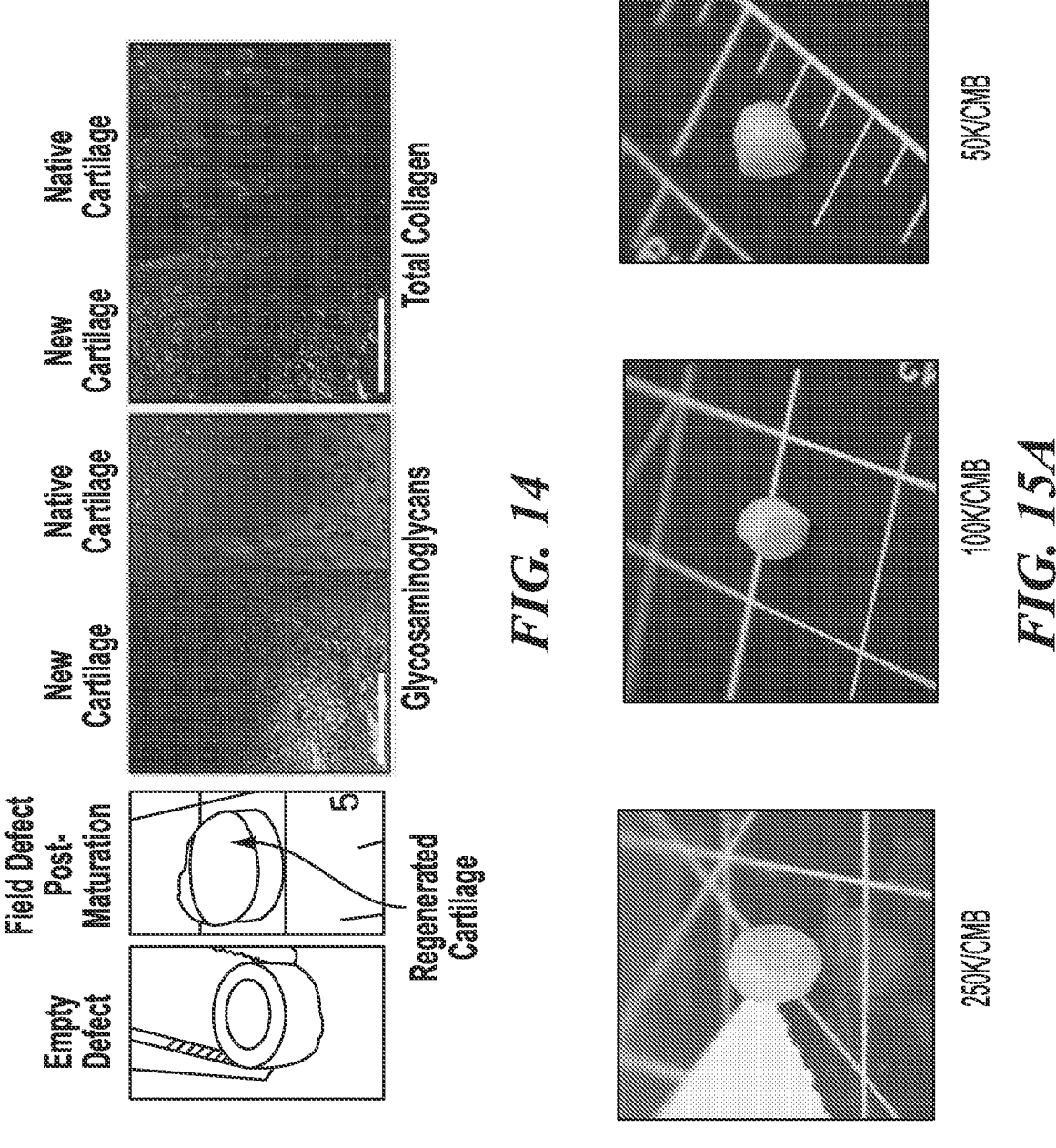
FIG. 14 shows the delivery of one hydrogel composition with CMBs to an explant defect. After ex vivo culturing, newly-formed tissue integrated to the native cartilage and exhibited glycosaminoglycan and collagen content comparable to native cartilage.
FIG. 15A shows cartilage constructs fabricated with multiple CMBs, hydrogels and growth factor. The tissue can be fabricated from multiple CMBs with various cell amounts, ranging from 50,000-250,000 cells/CMB.

In addition, a hydrogel composition with CMBs fabricated from ADSCs was delivered to an explant defect. Bovine osteochondral explants of 10 mm diameter and 10 mm thickness (cartilage thickness of 1-2 mm) were harvested from skeletally mature bovine knees. A biopsy punch was used to create a 5 mm diameter full thickness (down to the bone) defects. These defects were then filled with 1:1 volume mixture of CMBs and collagen/hyaluronan hydrogel and cultured in media containing TGF-β3 and BMP-6 growth factors for up to 5 weeks, with or without loading. After ex vivo culturing, newly-formed tissue integrated to the native cartilage and exhibited glycosaminoglycan and collagen content comparable to native cartilage. The data is shown in FIG. 14.

Example 13: Influence of CMB Size on Cartilage Construct Quality

Figure 15B:
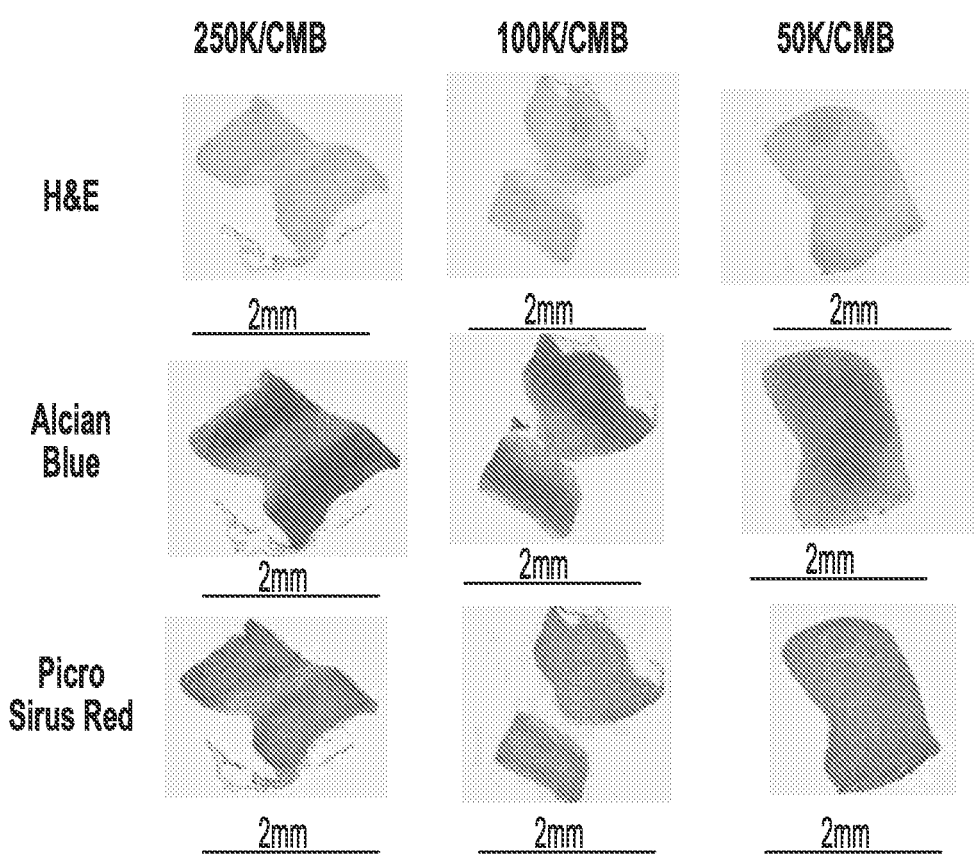
FIG. 15B shows histological staining of cartilage constructs fabricated with various CMB sizes. Results reveal comparable glycosaminoglycan and collagen content among experimental groups.

The effects of CMB size on cartilage construct quality were evaluated. CMBs were generated from 50K, 100K and 250K cells. Constructs were then fabricated with each CMB size, cultured for 4 weeks, and harvested for visual inspection, histology, and quantitative evaluation. Visual inspection revealed that samples in all experimental conditions exhibited well-fused CMBs. The data is shown in FIG. 15A. Moreover, constructs were opaque, which is indicative of cartilage-like quality. Histological staining for H&E confirmed visual observations, revealing fused CMBs in all groups, as shown in FIG. 15B. Histological staining for chondrogenic markers, GAG and collagen, showed comparable differentiation among experimental conditions. Quantitation of sample wet weight, DNA, GAG, and collagen were also compared across groups to identify how CMB size influences construct quality. The data is shown in FIG. 15C. For all parameters, values were relatively consistent among groups. These results indicate that 50K, 100K, and 250K CMB sizes all generate comparable cartilage quality and can be considered for cartilage filler product manufacturing.

REFERENCES

1. Riboh, J. C., et al., Comparative efficacy of cartilage repair procedures in the knee: a network meta-analysis. Knee Surg. Sports Traumatol. Arthrosc., 2016.
2. Goyal, D., et al., Evidence-based status of microfracture technique: a systematic review of level I and II studies. Arthroscopy, 2013. 29(9): p. 1579-88.
3. Brittberg, M., et al., Rabbit articular cartilage defects treated with autologous cultured chondrocytes. Clin. Orthop., 1996(326): p. 270-83.
4. Jacobi, M., et al., MACI—a new era? Sports Med Arthrosc. Rehabil. Ther. Technol., 2011. 3(1): p. 10.
5. Hangody, L., et al., Arthroscopic autogenous osteochondral mosaicplasty for the treatment of femoral condylar articular defects. A preliminary report. Knee Surg. Sports Traumatol. Arthrosc., 1997. 5(4): p. 262-7.
6. O'Driscoll, S. W., et al., The chondrogenic potential of free autogenous periosteal grafts for biological resurfacing of major full-thickness defects in joint surfaces under the influence of continuous passive motion. An experimental investigation in the rabbit. J. Bone Joint Surg. Am., 1986. 68(7): p. 1017-35.
7. Bobic, V., Current Status of the Articular Cartilage Repair. The Journal of Regenerative Medicine, 2000. 1(4): p. 37-41.
8. McNickle, A. G., et al., Overview of Existing Cartilage Repair Technology. Sports Med. Arthrosc. Rev., 2008. 16(4): p. 196-201.
9. Bobic, V., Tissue Repair Techniques of the Future: Options for Articular Cartilage Injury. Conference Report. Medscape Orthopaedics & Sports Medicine eJournal, 2000. 4(1).
10. Bos, P. K., et al., Articular cartilage repair and the evolving role of regenerative medicine. Open Access Surgery, 2010. 3: p. 109-122.
11. Rivera, J. C., et al., Posttraumatic Osteoarthritis Caused by Battlefield Injuries: The Primary Source of Disability in Warriors. J. Am. Acad. Orthop. Surg., 2012. 20(1): p. S64-69.
12. Anderson, D. D., et al., Post-traumatic osteoarthritis: improved understanding and opportunities for early intervention. J. Orthop. Res, 2011. 29(6): p. 802-809.
13. Olson, S., et al., Post-Traumatic Arthritis: Pathogenesis, Diagnosis and Management. 2015: Springer.
14. Hangody, L., et al., Autologous osteochondral grafting—technique and long-term results. Cartilage Repair, 2008. 39(1): p. 32-39.
15. Eichinger, J. K., et al., Penetrating Blast Injury to the Knee of a United States Soldier Treated with Allograft Mosaicplasty. Cartilage, 2011. 2(3): p. 307-311.
16. Scully, W. F., et al., Allograft Osteochondral Transplantation in the Knee in the Active Duty Population. Military Medicine, 2011. 176(10): p. 1196-1201.
17. Lima, E. G., et al., Functional tissue engineering of chondral and osteochondral constructs. Biorheology, 2004. 41(3-4): p. 577-90.
18. Hu, J. C., et al., A self-assembling process in articular cartilage tissue engineering. Tissue Eng., 2006. 12(4): p. 969-79.
19. Bhumiratana, S., et al., Large, stratified, and mechanically functional human cartilage grown in vitro by mesenchymal condensation. Proc. Natl. Acad. Sci. USA, 2014. 111(19): p. 6940-5.
20. McIntosh, K. R., et al., Evolution and future prospects of adipose-derived immunomodulatory cell therapeutics. Expert Rev. Clin. Immunol., 2013. 9(2): p. 175-84.
21. Yodmuang, S., et al., Synergistic effects of hypoxia and morphogenetic factors on early chondrogenic commitment of human embryonic stem cells in embryoid body culture. Stem Cell Rev., 2015. 11(2): p. 228-41.
22. Ryan, J. M., et al., Mesenchymal stem cells avoid allogeneic rejection. J. Inflamm. (London), 2005. 2: p. 8.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method comprising:

isolating stem cells from an allogenic source or an autologous source;

culturing the stem cells in a chondrogenic medium until they form one or more condensed mesenchymal cell bodies (CMBs);

freezing the CMBs at a temperature of less than about −80° C. at an immature state; and storing the CMBs, at the temperature of less than about −80° C. and at an immature state, for at least one day at an immature state, wherein a CMB at the immature state is a CMB that has been cultured for fewer than six days prior to freezing and storing at the temperature of less than about −80° C., wherein the CMBs, after thawing, are configured to mature in vivo and are effective to form cartilage in a site of a tissue defect, and wherein the cartilage is integrated with surrounding connective tissue.

2. The method of claim 1, wherein the CMBs comprise a cell volume of at least 50,000 cells/ML of medium.

3. The method of claim 1, wherein:

the cartilage is articular cartilage; and the tissue defect is a cartilage defect, cartilage degradation, cartilage injury, cartilage degenerative disease or cartilage disorder.

4. The method of claim 1, wherein isolating the stem cells comprises at least one of isolating stromal vascular fraction (SVF) from adipose tissue or isolating bone marrow-derived stem cells (BMSCs) from bone marrow tissue.

5. The method of claim 1 further comprising:

thawing the CMBs; and combining the CMBs with a hydrogel to treat the tissue defect.

6. The method of claim 1, wherein the method is effective to form tissue comprising at least 3% (w/w) glycosaminoglycan (GAG) in the site of the tissue defect.

7. The method of claim 1, wherein the cartilage comprises a Young's modulus of at least 100 kPa and a friction coefficient of at most 0.8 in the site of the tissue defect.

8. The method of claim 1, wherein the cartilage comprises at least 2% (w/w) collagen in the site of the tissue defect.

9. The method of claim 1 further comprising:

combining the CMBs with a hydrogel after thawing the CMBs from storage at the immature state;

placing the combination of CMBs and the hydrogel into a syringe; and injecting the combination of the CMBs and the hydrogel into the site of the tissue defect.

10. The method of claim 9 further comprising adding growth factor to the combination of the CMBs and the hydrogel, wherein the growth factors are encapsulated in a polymer microsphere, wherein the polymer microsphere comprises poly (lactic-co-glycolic acid) (PLGA), poly (lactic acid) (PLA), or a combination of PLGA and PLA, and wherein the growth factor is a TGF-β superfamily member or is a morphogenic protein selected from the group consisting of OP-1, OP-2, OP-3, TGF-β1, TGF-β2, TGF-β3, TGF-β4, BMP-1, BMP-2, BMP-3, BMP-4, BMP-5, BMP-6, BMP-8, BMP-9, BMP-10, BMP-11, BMP-12, BMP-13, BMP-15, BMP-16, BMP-17, BMP-18, DPP, Vg1, Vgr-1, 60A protein, GDF-1, GDF-2, GDF-3, GDF-5, GDF-6, GDF-7, GDF-8, GDF-9, GDF-10, GDF-11, GDF-12, CDMP-1, CDMP-2, CDMP-3, NODAL, UNIVIN, SCREW, ADMP, NEURAL.

11. The method of claim 1, wherein the cartilage is selected from the group consisting of nasal cartilage, auricular cartilage, tracheobronchial cartilage, costal cartilage, a meniscus and an intervertebral disc.

* * * * *